US006749592B2

(12) United States Patent
Lord

(10) Patent No.: US 6,749,592 B2
(45) Date of Patent: *Jun. 15, 2004

(54) SUCTION PRESSURE REGULATOR FOR USE WITH A CHEST DRAINAGE

(76) Inventor: Kevin M. Lord, 18 Cotuit Rd., East Tauton, MA (US) 02718

( * ) Notice: Subject to any disclaimer, the term of this patent is extended or adjusted under 35 U.S.C. 154(b) by 0 days.

This patent is subject to a terminal disclaimer.

(21) Appl. No.: 10/213,141

(22) Filed: Aug. 5, 2002

(65) Prior Publication Data

US 2002/0193761 A1 Dec. 19, 2002

Related U.S. Application Data

(63) Continuation of application No. 09/336,471, filed on Jun. 18, 1999, now Pat. No. 6,447,491.

(51) Int. Cl.$^7$ .................................................. A61M 1/00
(52) U.S. Cl. ...................................... 604/319; 604/317
(58) Field of Search .............................. 604/319–328; 137/247.19; 251/901, 61.1, 63.5, 61.3, 61.5

(56) References Cited

U.S. PATENT DOCUMENTS

| 2,318,157 | A | 5/1943 | Heiser |
| 2,587,375 | A | 2/1952 | Paulsen |
| 2,737,167 | A | 3/1956 | Dickey |
| 3,100,002 | A | 8/1963 | Moore |
| 3,363,627 | A | 1/1968 | Bidwell et al. |
| 3,545,440 | A | 12/1970 | Mishkin et al. |

(List continued on next page.)

FOREIGN PATENT DOCUMENTS

| DE | 2148331 | 10/1970 |
| DE | 2351709 | 11/1972 |
| EP | 0096579 | 12/1983 |
| EP | 0112641 | 7/1984 |
| FR | 1035675 | 8/1953 |
| GB | 2141933 | 1/1985 |
| WO | WO 97/14449 | 4/1997 |

OTHER PUBLICATIONS

Understanding Chest Drainage, Deknatel, Inc., Publication, Jul., 1995. Rev. C.
Deknatel Product Literature, Pleur–Evac Plus A9250; Sep., 1994.

(List continued on next page.)

Primary Examiner—John J. Calvert
Assistant Examiner—Michele Kidwell
(74) Attorney, Agent, or Firm—John W. Ryan Dechert, LLP

(57) ABSTRACT

Featured is a pressure control regulator including a housing, a sealing member disposed within the housing, a flexible member and a biasing mechanism. The housing includes at least one inlet aperture and at least one outlet aperture, each inlet aperture being fluidly coupled to a first pressure source and each outlet aperture being fluidly coupled to a second pressure source, the first and second pressure sources being at different pressures. The flexible member extends between the sealing member outside surface and the housing inner surface so as to form a pressure boundary therebetween and to divide the housing interior into first and second compartments. The biasing mechanism, being responsive to pressure within the second compartment, acts on the sealing member so the sealing member is in one of an open position, when the second compartment is greater than a predetermined pressure value, or a closed position, when the second compartment pressure is at or below the predetermined pressure value. A portion of the housing in fluid communication with the second pressure source, also includes a mechanism to restrict fluid flow to or from the second compartment such that the second compartment pressure changes when fluid flow in either direction occurs for a time more than a predetermined period of time and remains effectively unchanged when such fluid flow time is less than the predetermined period of time. In a more particular embodiment, the second pressure source is a suction source and the regulator is a suction pressure regulator.

40 Claims, 9 Drawing Sheets

U.S. PATENT DOCUMENTS

| | | | |
|---|---|---|---|
| 3,552,395 | A | 1/1971 | Bidwell et al. |
| 3,559,647 | A | 2/1971 | Bidwell et al. |
| 3,683,913 | A | 8/1972 | Kurtz et al. |
| 3,739,797 | A | 6/1973 | Caldwell |
| 3,782,497 | A | 1/1974 | Bidwell et al. |
| 3,784,144 | A | 1/1974 | Ollinger et al. |
| 3,809,085 | A | 5/1974 | Bidwell et al. |
| 3,812,855 | A | 5/1974 | Banko |
| 3,830,238 | A | 8/1974 | Kurtz et al. |
| 3,996,955 | A | 12/1976 | Kawabata |
| 4,015,603 | A | 4/1977 | Kurtz et al. |
| 4,018,224 | A | 4/1977 | Kurtz et al. |
| 4,032,263 | A | 6/1977 | Pareja |
| D245,372 | S | 8/1977 | Kurtz et al. |
| 4,092,998 | A | 6/1978 | Taplin |
| 4,105,031 | A | 8/1978 | Kurtz et al. |
| 4,112,948 | A | 9/1978 | Kurtz et al. |
| D250,207 | S | 11/1978 | Kurtz et al. |
| RE29,877 | E | 1/1979 | Kurtz et al. |
| 4,258,824 | A | 3/1981 | Kurtz et al. |
| 4,299,373 | A | 11/1981 | Troyer |
| 4,439,189 | A | 3/1984 | Sargeant et al. |
| 4,444,548 | A | 4/1984 | Andersen et al. |
| 4,445,884 | A | 5/1984 | Kurtz et al. |
| 4,456,218 | A | 6/1984 | Kawabata et al. |
| 4,458,712 | A | 7/1984 | Stevenson |
| 4,497,335 | A | 2/1985 | Masuda |
| 4,499,916 | A | 2/1985 | Hanson et al. |
| 4,534,765 | A | 8/1985 | Todd et al. |
| 4,544,370 | A | 10/1985 | Elliott et al. |
| 4,550,749 | A | 11/1985 | Krikorian |
| 4,596,264 | A | 6/1986 | Gladstone et al. |
| 4,605,400 | A | 8/1986 | Kurtz et al. |
| 4,614,168 | A | 9/1986 | Batchelor |
| 4,650,476 | A | 3/1987 | Telang |
| 4,658,834 | A | 4/1987 | Blankenship et al. |
| 4,698,060 | A | 10/1987 | D'Antonio et al. |
| 4,715,855 | A | 12/1987 | D'Antonio et al. |
| 4,715,856 | A | 12/1987 | Elliott et al. |
| 4,718,895 | A | 1/1988 | Kurtz et al. |
| 4,723,891 | A | 2/1988 | Takenaka et al. |
| 4,738,671 | A | 4/1988 | Elliott et al. |
| 4,747,843 | A | 5/1988 | Felix et al. |
| 4,747,844 | A | 5/1988 | Elliott et al. |
| 4,756,501 | A | 7/1988 | Quercia et al. |
| 4,784,642 | A | 11/1988 | Everett, Jr. et al. |
| 4,830,047 | A | 5/1989 | Hodge |
| 4,857,042 | A | 8/1989 | Schneider |
| 4,889,531 | A | 12/1989 | D'Antonio et al. |
| 4,903,726 | A | 2/1990 | Martin et al. |
| 4,913,107 | A | 4/1990 | Schweiger |
| 4,921,014 | A | 5/1990 | Tartaglia et al. |
| 4,955,873 | A | 9/1990 | Rajlevsky |
| 4,955,874 | A | 9/1990 | Farrar et al. |
| 4,973,180 | A | 11/1990 | Hori |
| 5,026,358 | A | 6/1991 | Everett, Jr. et al. |
| 5,076,322 | A | 12/1991 | Choksi et al. |
| 5,078,174 | A | 1/1992 | Grooms et al. |
| D324,102 | S | 2/1992 | Farrar et al. |
| 5,141,504 | A | 8/1992 | Herweck et al. |
| 5,236,425 | A | 8/1993 | Kurtz et al. |
| 5,286,262 | A | 2/1994 | Herweck et al. |
| 5,299,683 | A | 4/1994 | Poole |
| 5,300,050 | A | 4/1994 | Everett, Jr. et al. |
| 5,318,510 | A | 6/1994 | Cathcart |
| 5,326,069 | A | 7/1994 | Clear et al. |
| 5,335,655 | A | 8/1994 | Kee |
| 5,346,373 | A | 9/1994 | Riffe |
| 5,380,314 | A | 1/1995 | Herweck et al. |
| 5,449,347 | A | 9/1995 | Preen et al. |
| 5,458,567 | A | 10/1995 | Cathcart |
| 5,480,116 | A | 1/1996 | Callas |
| 5,499,789 | A | 3/1996 | Rose |
| 5,507,734 | A | 4/1996 | Everett, Jr. et al. |
| 5,577,897 | A | 11/1996 | Inagaki et al. |
| 5,624,417 | A | 4/1997 | Cook et al. |
| 5,636,975 | A | 6/1997 | Tiffany et al. |
| 5,674,390 | A | 10/1997 | Matthews et al. |
| 5,680,977 | A | 10/1997 | Burke |
| 5,807,358 | A | 9/1998 | Herweck et al. |
| 5,931,821 | A | 8/1999 | Weilbacher et al. |
| 5,989,234 | A | 11/1999 | Valerio et al. |
| 6,024,120 | A | 2/2000 | Yam et al. |
| 6,062,823 | A | 5/2000 | Kawaguchi et al. |
| 6,070,582 | A | 6/2000 | Kee |

OTHER PUBLICATIONS

Deknatel Product Literature, Pleur–Evac Plus A–6000; Dec., 1995.

Deknatel Product Literature, Pleur–Evac Plus A–7000 Series; 1994.

Deknatel Product Literature, Pleur–Evac A–8000 Series; Sep., 1993.

Code No. A–6000–Pleur–Evac, Adult–Pediatric Single Use Chest Drainage Unit Dry Suction Control Autotransfusion Compatible With Code No. A–1500, Instructions For Use, Deknatel, Inc., Stock P/N: 131119, Issue Date: Apr. 1997.

Code No. A–6002–Pleur–Evac, Adult–Pediatric Dual Collection Chest Drainage System Dry Suction Control With Autotransfusion Option Compatible With Code No. A–1500, Instructions For Use, Deknatel, Inc., Part No. 115322, Date Issued: Feb. 1994.

Code No. 0077000–Deknatel, Thora–Klex, Chest Drainage System 2500ML Collection Unit, Instructions For Use, P/N 123581, Issue Date: Oct. 1996.

Code No. 0077020–Deknatel, Thora–Klex, Chest Drainage System 4000ML Dual Collection, Instructions For Use, P/N 123583, Issue Date: Oct. 1996.

Code No. 007030–Deknatel, Thora–Klex, Chest Drainage System 350 ML Collection Unit, Instructions For Use, P/N 123586, Issue Date: Oct. 1996.

Code No. S–1100A–Genzyme Surgical Products, Pleur–Evac Sahara, Chest Drainage System.

Code No. S–1100A–Genzyme Surgical Products, Pleur–Evac Sahara, Chest Drainage System, Autotransfusion Instructions, Copyright 1999.

Code No. S–1150A–Genzyme Surgical Products, Pleur–Evac Sahara, Continuous Reinfusion Autotransfusion System.

Code No. S–1150A–Genzyme Surgical Products, Pleur–Evac Sahara Plus, Continuous Reinfusion Autotransfusion System, Continuous Reinfusion Set–Up, Copyright 1999.

Zuhdi, Nazih, M.D. et al., Vacuum Regulator For Cardiotomy Return And Chest Drainage Systems, J. Thoracic Cardiologic Surgery, vol. 39, No. 2, Feb. 1960, pp. 221–224.

SUCTION PRESSURE REGULATOR FOR USE WITH A CHEST DRAINAGE

The present application is a continuation of U.S. application Ser. No. 09/336,471 filed on Jun. 18, 1999 now U.S. Pat. No. 6,447,491.

FIELD OF INVENTION

The present invention relates to drainage devices and systems and more particularly to suction drainage systems and devices for removing gases and/or liquids from medical patients, such as from the pleural cavity, by means of a pressure differential.

BACKGROUND OF THE INVENTION

For many years, the standard apparatus for performing the evacuation of the pleural cavity was a drainage system known as the "3-bottle set-up" which includes a collection bottle, a water seal bottle and a suction control bottle. A catheter runs from the patient's pleural cavity to the collection bottle, and the suction bottle is connected by a tube to a suction source. The three bottles are connected in series by various tubes to apply suction to the pleural cavity to withdraw fluid and air and thereafter discharge the same into the collection bottle. Gases entering the collection bottle bubble through water in the water seal bottle. The water in the water seal bottle also usually prevents the back flow of air into the chest cavity.

The suction pressure (vacuum) and pressure differentials must be precisely maintained with the "3-bottle set-up" because of the dangerous conditions that could result if unduly high or low pressure differentials should occur. Complications such as pneumothorax may result from the loss of the water seal in the water seal bottle if suction were temporarily disconnected, and undue build-ups of positive pressure could cause tension pneumothorax and possible mediastinal shift. To accomplish this precise control, however, results in increased maintenance and monitoring. For example, evaporation in the suction control chamber or bottle results in suction pressure variations which must be corrected by the addition of more water by a nurse, doctor or other authorized medical personnel.

The 3-bottle set-up lost favor with the introduction of an underwater seal drainage system sold under the name "PLEUR-EVAC"® in 1966 by Deknatel Inc. U.S. Pat. Nos. 3,363,626; 3,363,627; 3,559,647; 3,683,913; 3,782,497; 4,258,824; and Reissue 29,877 are directed to various aspects of the PLEUR-EVAC® system which over the years has provided improvements that eliminated various shortcomings of the 3-bottle set-up. These improvements have included the elimination of variations in the 3-bottle set-up that existed between different manufacturers, hospitals and hospital laboratories. A more detailed description of the need for and the proper use of chest drainage devices is presented in the Deknatel Inc. PLEUR-EVAC® publication entitled "Physiology of the Chest and Thoracic Catheters; Chest Drainage Systems No. 1 of a series from Deknatel" (1985) which is incorporated herein by reference. Among the features of the PLEUR-EVAC®) system which provide its improved performance is a single, pre-formed, self-contained unit that embodies the 3-bottle techniques. These PLEUR-EVAC® systems are sometimes referred to as wet or wet—wet chest drainage systems because they employ a fluid such as water both for suction control (i.e., a water manometer) and to establish the patient seal.

Despite the advantages of the PLEUR-EVAC® drainage system over the 3-bottle set-up and the general acceptance of this device in the medical community, improving the convenience and performance capabilities of chest drainage systems continues. One such improvement involved replacing the water filled manometer used for suction control with a dry or waterless suction control regulator, such as that described in U.S. Pat. Nos. 5,026,358; 5,300,050; 4,784,642 and 5,807,358. In these systems the dry suction control regulator includes a mechanism, such as a spring-loaded valve, to control the suction pressure and a water filled chamber is interposed between the suction source and the collection chamber, thereby forming the patient seal.

In these drainage devices or systems, the suction pressure actually being applied, however, could cause rapid modulation of the spring-loaded valve as a consequence of the suction pressure differentials or changes that occur during normal operation. For example, such suction pressure differentials can result from the cyclical pressure variations occurring in the suction source (e.g., suction pump). Such rapid modulation of the valve can cause the device or system to emanate a humming sound or other noise that would make the device or system unsuitable as a practical matter for the intended use (e.g. in a hospital). In order to reduce or attenuate this modulation, and thus also reduce or attenuate the unwanted sound, the drainage devices or systems are configured with a means or mechanism to dampen the rapid modulation of the valve.

In one exemplary case, such as that described in U.S. Pat. Nos. 5,026,358 and 4,784,642, attenuation of the rapid modulation of the valve in the suction control regulator is accomplished by means of a dashpot. The dashpot includes a plug that is interconnected to the plate valve member and which rides within a well. In the described embodiment, the plug is made from graphite and the well is formed of a glass annulus, which together provide non-binding surfaces so as to avoid the sticking of the component parts.

In order for the dashpot to function in the intended manner it is necessary for the plug and well to be manufactured with a high tolerance of perpendicularity. As a practical matter, this means that the plug and the member including the well must be manufactured to rather precise tolerances on the order of millionths of an inch. In addition, it is not uncommon for the plug and the member including the well to be further sorted and segregated so as to establish pairs of parts that can be used to make an acceptable dashpot, thereby minimizing wastage. Consequently, the dashpot and the components thereof are labor intensive and expensive to make.

Another type of drainage device, such as that described in U.S. Pat. Nos. 4,738,671; 4,715,856, 4,544,370; and 4,747,844, includes a modulation valve to control the suction flow, and correspondingly the suction pressure being developed, and a one way valve that forms the seal between the suction source and the collection chamber (e.g. the patient seal). These units are complex and involve a large number of parts.

It thus would be desirable to provide a waterless suction pressure regulator that includes a suction pressure control device that controls or regulates the suction pressure being applied to the waterless suction regulator. It would be particularly desirable to provide a suction pressure regulating device that would attenuate or control changes in suction pressure that could lead to rapid modulation while allowing the suction pressure regulator to be responsive to physiological induced suction pressure changes as well as long term suction source pressure changes. Such a suction pressure regulating device, and drainge devices and systems utilizing such a pressure regulating device preferably would be simple in construction and less costly than prior art devices and the methods related thereto would not require highly skilled users to utilize the device.

SUMMARY OF THE INVENTION

The present invention features a novel device, a suction pressure regulator for controlling the suction pressure being developed within the devices used for draining gases and/or liquid from the body cavity. The drainage of liquid, blood, and/or gas from the body cavity is accomplished by establishing a pressure differential between the device and the body cavity to be drained and maintaining or controlling this pressure differential at a desired value by means of the suction pressure regulator. Also featured is a pressure control regulator for use in combination with a medical device. Further featured are methods related to such a differential pressure control device and/or devices, apparatuses or systems using such differential pressure control device. Various aspects or features of the suction pressure regulator of the present invention, as well as the drainage devices using such a suction pressure regulator, provide a number of benefits as compared to prior art devices.

In a first aspect, the suction pressure regulator according to the present invention included a housing having at least one inlet aperture and at least one outlet aperture, a flexible member, a sealing member disposed with the housing and a biasing mechanism. Each of the at least one inlet aperture is in fluid communication with a pressurized gas source such as the atmosphere and the each of the at least one outlet aperture is in fluid communication with a suction source.

The flexible member extends between an outside surface of the sealing member and an inner surface of the housing so as to form a pressure boundary between the sealing member and the housing and so as to divide the interior of the housing into a first and a second compartment.

The biasing mechanism acts on the sealing member so as to selectively urge a portion of the sealing member against the housing inner surface proximal and about the at least one inlet aperture to form a seal between the at least one inlet aperture and the at least one outlet aperture, when the pressure in the housing second compartment is at or below a predetermined pressure value. Also, when the pressure in the second compartment is above a predetermined pressure value, the biasing mechanism is configured so as to allow the sealing member to move away from the housing inner surface so as to put each of the at least one inlet aperture in fluid communication with each of the at least one outlet aperture, whereby the pressurized gas source is put into fluid communication with the suction source.

Additionally, a portion of the housing that is in fluid communication with the second compartment and the suction source includes a flow regulating mechanism that restricts or controls the flow of fluid to and from the second compartment, so as to effectively control changes in pressure within the second compartment. In this way, only fluid flow to or from the second compartment that occurs for more than a given period of time can cause a change in the pressure within the second compartment. Whilst fluid flow to or from the second compartment that occurs for less than the given period or amount of time does not effectively change the pressure within the second compartment.

In particular embodiments, the flow regulating mechanism includes a porous plug, an orifice, a tortuous flow path or other means known to those skilled in the art for restricting flow, one end of which is positioned so as to be in fluid communication with the second compartment and the other end of which is positioned so as to communicate with the suction pressure source. In a more specific embodiment, the housing includes a through aperture positioned so as to be in fluid communication with the second compartment and the flow regulating mechanism comprises a porous plug that is disposed within the through aperture. The porosity of the plug is set or established so as to control the fluid flow to/from the second compartment.

In a second aspect, the biasing mechanism of the suction pressure regulator comprises a means for tensioning the sealing member closed when the pressure developed in the housing second compartment is at or below the predetermined pressure value and otherwise opening the sealing member so as to fluidly couple the pressurized gas source (e.g. ambient or atmosphere) with the suction source. Preferably, the tensioning means comprises a spring under tension and coupled at one end to the sealing member and at its other end to a support member, so as to maintain the sealing member in a closed sealing relationship with the at least one inlet aperture in accordance with the predetermined pressure value.

Also provided is means for adjusting the spring tension in predetermined preset discrete steps so as to provide one of a predetermined pressure value. Preferably, the adjusting means comprises a worm gear disposed on at least a portion of the support member; pinion gear being rotatably supported and cooperatively engaging the worm gear; dial coupled to the pinion gear and having a plurality of predetermined preset grooves along its periphery; detent member resiliently disposed against the periphery and configured and dimensioned for seating within one of the grooves and such that upon rotating the dial, the detent member rides along the periphery until seating within one of the next grooves.

The biasing mechanism according to a second aspect of the present invention further comprises means for variably calibrating the tension of the spring while the detent member is seated within one of the predetermined preset grooves of the dial so that the spring tension can be selectively varied without any rotation of the dial. In one preferred embodiment, the tension calibration means comprises a rotatable collar, the other end of the support member being secured to the collar for rotation therewith so that upon rotation of the collar together with the support member, the tension of the spring can be selectively varied while the dial is stationary. At least a portion of the dial is disposed so that the dial can be rotated externally by a user. The dial has graduations thereon to indicate the suction pressure imposed in the collection chamber while the detent member is seated in one of the grooves.

Alternatively, the biasing mechanism comprises a spring that is disposed so as to be between a lower surface of the sealing member and a lower inside surface of the housing. In this way, the spring urges the sealing member against the housing inner surface when the pressure in the housing second compartment is at or below the desired pressure value. When the pressure within the housing second compartment is greater than the desired value, the spring force is overcome causing the spring to compress and thereby allowing the sealing member to move away from the housing inner surface. The spring is preferably pre-compressed to a value corresponding to the pre-determined pressure value.

In a third aspect, there is featured a pressure control regulator that includes a housing, a sealing member moveably disposed within the housing, a flexible member and a biasing mechanism. The housing includes at least one inlet aperture and at least one outlet aperture, where each of the at least one inlet aperture is in fluid communication with a first pressure source and each of the at least one outlet aperture is in fluid communication with a second pressure source, the first pressure source being at a different pressure from the second pressure source.

The flexible member extends between an outside surface of the sealing member and an inner surface of the housing so as to form a pressure boundary therebetween and to divide an interior of the housing into first and second compartments. The biasing mechanism is responsive to pressure within the housing second compartment and acts on the sealing member so the sealing member is in one of an open position, when the pressure within the housing second compartment is greater than a predetermined pressure value, or a closed position, when the pressure therein is at or below the predetermined pressure value. In other words the biasing mechanism is responsive to the differential pressure between the housing first and second compartments.

In particular embodiments, the biasing mechanism is arranged so that in the closed position a sealing portion of the sealing member is urged against the housing inner surface so as to form a seal between each of the at least one inlet aperture and each of the at least one outlet aperture. Further, the biasing mechanism is arranged so that in the open position the sealing member is moved away from the chamber inner surface whereby each of the at least one inlet aperture is put into fluid communication with each of the at least one outlet aperture.

Also, a portion of the housing that is in fluid communication with the second pressure source, includes a mechanism to restrict the flow of fluid to or from the housing second compartment. This flow restricting mechanism restricts fluid flow such that the pressure within the housing second compartment is changed when the fluid flow in either direction occurs for a time more than a predetermined period of time and remains effectively or essentially unchanged when the flow of fluid in either direction is for a time less than the predetermined period of time. In this way, the sealing member is not responsive to fluid flow changes that are nor for more than a predetermined period of time.

Reference also should be made to the foregoing discussion for the suction pressure regulator for other aspects, arrangements or configurations of the above identified features of the pressure control regulator that correspond thereto.

In a fourth aspect, there is featured a drainage device according to the present invention for draining gases and/or liquids from a body cavity including at least two chambers, a suction pressure regulation chamber and a collection chamber that are fluidly interconnected. The collection chamber includes a port that is in fluid communication with the area or region to be drained.

The pressure regulation chamber is fluidly coupled to a source of pressurized gas, such as the atmosphere, and fluidly coupled to a suction source. The pressure regulation chamber also includes a suction pressure regulator device as described above that selectively adjusts the negative pressure or degree of vacuum being developed within the collection chamber and maintains the negative pressure or degree of vacuum being applied at or about a selected value.

More specifically the at least one inlet aperture of the suction pressure regulator is fluidly coupled to the pressurized gas source, the at least one outlet aperture, along with the housing portion in fluid communication with the second compartment, is fluidly coupled to the suction source. The biasing mechanism urges a portion of the sealing member against the housing inner surface proximal and about the at least one inlet aperture to form a seal between the at least one inlet aperture and the at least one outlet aperture, when the pressure in the housing second compartment is at or below a predetermined suction pressure value. Also, when the pressure in the second compartment is above or greater than the predetermined suction pressure value (i.e., more negative), the biasing mechanism is configured so as to allow the sealing member to move away from the housing inner surface so as to put each of the at least one inlet aperture in fluid communication with each of the at least one outlet aperture. Whereby the pressurized gas source or the atmosphere is put into fluid communication with the suction source so as to maintain the negative pressure being developed within the collection chamber at the desired value.

In a fifth aspect, the drainage device according to the present invention includes a patient seal, being interposed between the pressure regulation chamber and the collection chamber, and a venting or flow path arrangement that is interposed between the collection chamber and the patient seal. The flow path is arranged to prevent fluids accumulating in the collection chamber from being communicated upstream to other parts of the drainage device in the event that the device falls onto its front side or its backside.

In particular embodiments, the venting arrangement includes an intermediate chamber positioned proximate the backside of the drainage device and at least two flow passages. One flow passage fluidly couples the intermediate chamber and the collection chamber and another flow passage fluidly couples the intermediate chamber to the flow path going to the patient seal. In a preferred embodiment, two spaced flow passages fluidly couple the intermediate chambers and the collection chamber. These flow passages are also arranged so each is in a front-to-back type of relationship or to be essentially perpendicular to the front surface of the device.

In a sixth aspect, the patient seal of the drainage device of the present invention is configured so as to be either a wet or a dry patient seal. When configured as a wet patient seal, the drainage device further includes a third chamber, one end of which being fluidly coupled to the pressure regulation chamber and another end of which being fluidly coupled to the collection chamber. The third chamber is configured so as to include a sufficient quantity of fluid and to provide an adequate fluid level so that a fluid seal is formed and maintained at least when the suction pressure being developed in the collection chamber is at or below the desired value.

When configured as a dry patient seal, the drainage device further includes a one-way valve such as a high precision flapper type check valve. Such a valve preferably is configured so as to open at relatively low differential pressures and functions independent of any fluid collected in the collection chamber. In a particualr embodiment, the check valve opens at a pressure differential of about 0.5 cm of $H_2O$.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference characters denote corresponding parts throughout the several views and wherein.

DESCRIPTION OF THE PREFERRED EMBODIMENT

Figure 1:
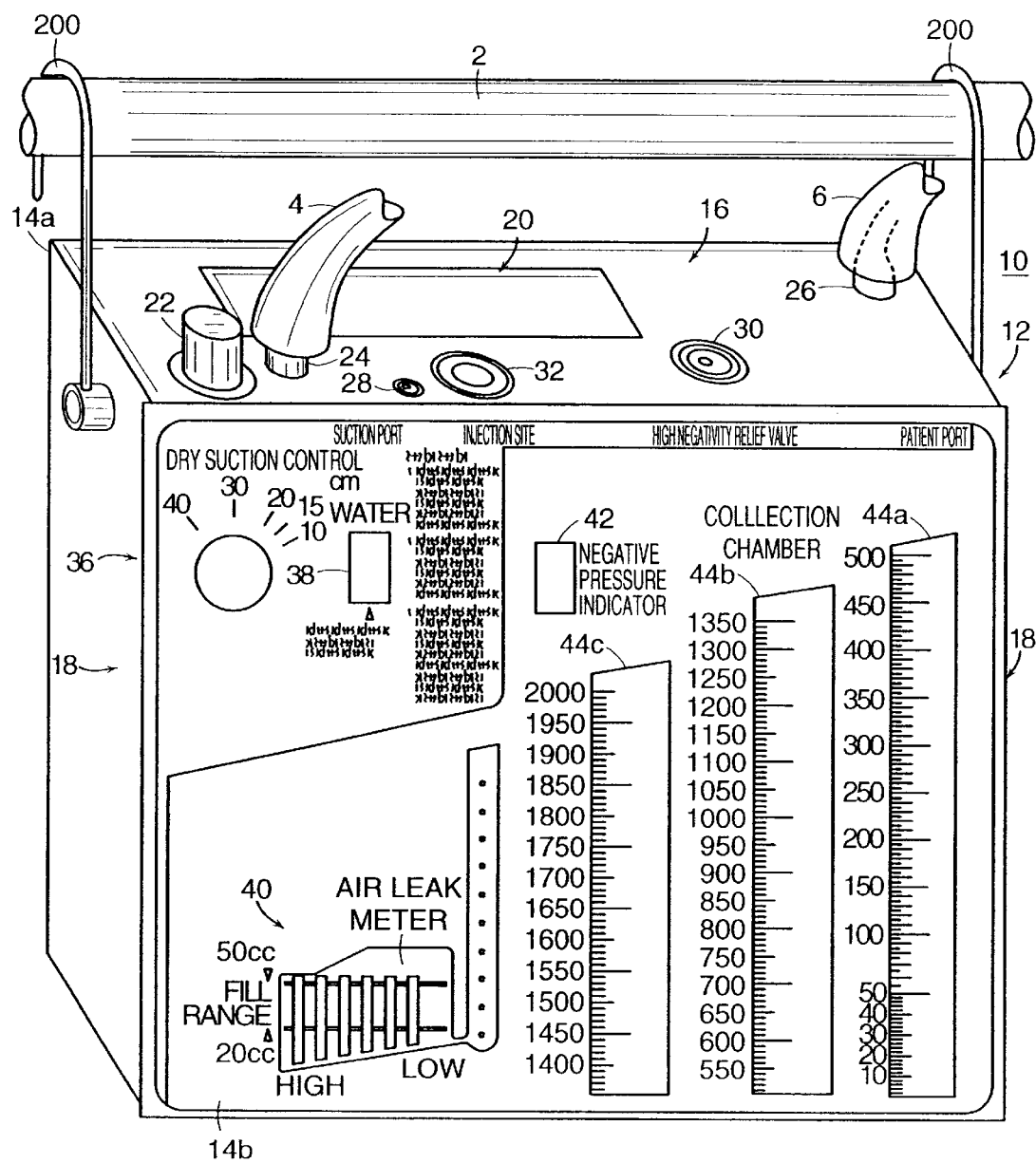
FIG. 1 is an axonometric schematic view of one drainage device according to the present invention.
Figure 2:
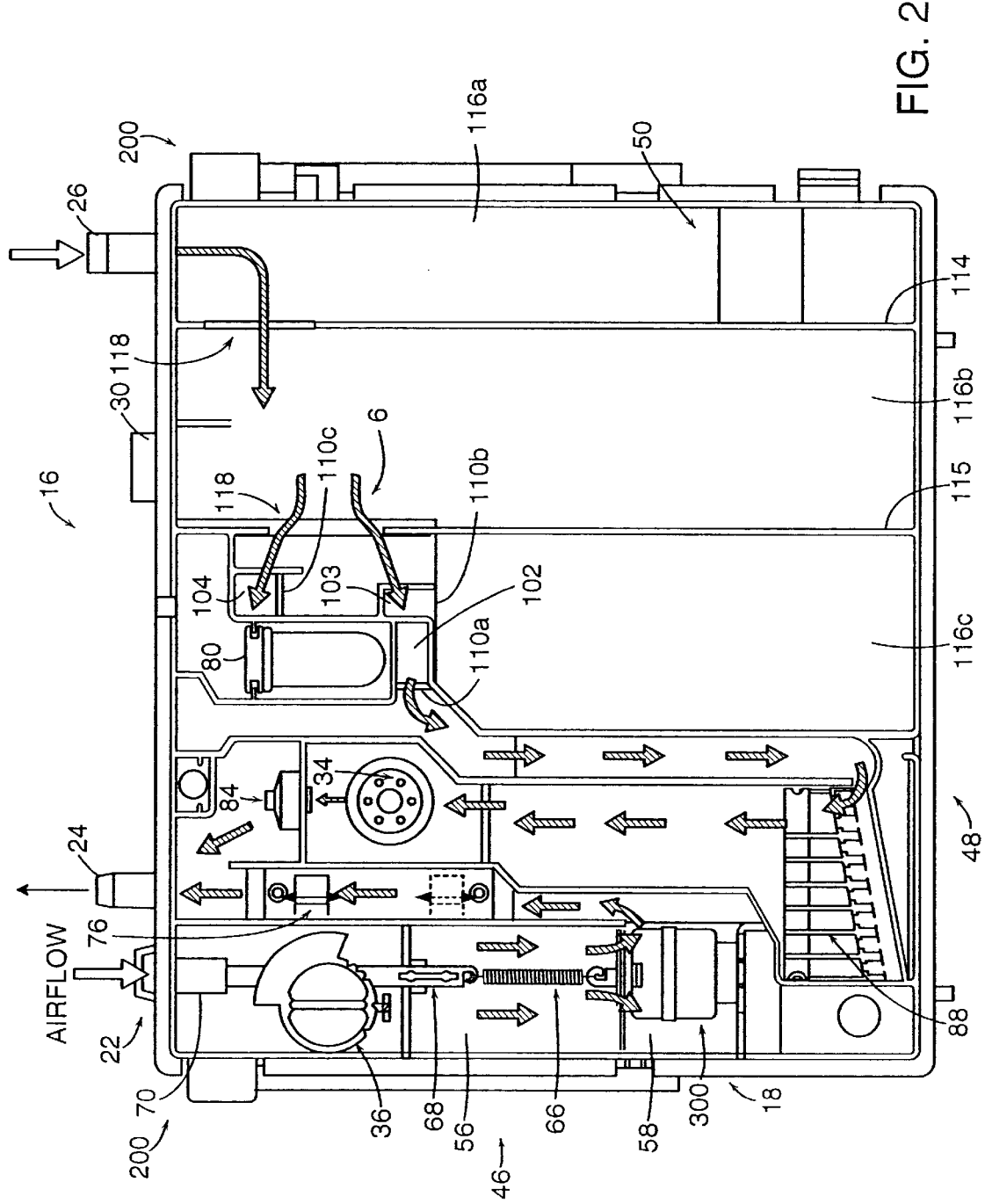
FIG. 2 is a cross-sectional front view of the drainage device of FIG. 1 showing a rolling seal suction pressure regulator according to the present invention with the front panel removed for clarity.

Referring now to the various figures of the drawing wherein like reference characters refer to like parts, there is shown in FIGS. 1–2 a drainage device 10 that can be used to drain gases and liquids from the body cavity of a medical patient (not shown). In one arrangement, the drainage device is hung from a support, such as the side rail 2 of a hospital bed, by means of two hangers 200 rotatably attached to the sides 18 of the device housing 12. The drainage device housing 12 also is formed so the device 10 can be self-supporting or self-standing, however, it is within the scope of the present invention for the device housing to be configured with a floor stand (e.g., see FIG. 7) to further improve the device's overturning moment. For further details of the construction, materials and operational characteristics of the drainage device 10, excluding the rolling seal suction pressure regulator 300 of the present invention, reference should be made to U.S. Ser. No. 08/783,177 the teachings of which are incorporated herein by reference.

In use, the drain line 6 from the patient is connected to the patient port 26 of the device housing 12 and the patient's thoracic catheter. Also, the suction line 4 is interconnected to the source of negative pressure, the suction source, and to the suction port 24. The suction and patient ports 24,26 are located in the device housing 12 so the suction port is in fluid communication with the suction pressure regulation chamber 46 of the device 10 and so the patient port 26 is in fluid communication with the collection chamber 50.

The device housing 12 is a unitary housing formed from two portions, a rear or body portion 14a and a front panel 14b. The body portion 14a is molded preferably using a light colored opaque plastic material and is constructed with a number of walls, posts and other like structures which generally extend to the front panel 14b so as to define a plurality of chambers, ribs, compartments and support elements. The front panel 14b is formed from a transparent sheet of plastic material having a substantially uniform thickness.

As illustrated more clearly in FIG. 1, a graphic mask is typically printed on the front panel 14b and includes a plurality of windows, status indicators, and calibration or measuring indicia, as well as other information provided for the user. Alternatively, a label or mask may be applied using any of a number of techniques known to those skilled in the art. Among the so-called windows defined by the mask, are a suction status window 38, an air leak meter window 40 and a negative pressure indicator window 42 that are aligned over the corresponding chamber or compartment of the device 10. Also provided are a plurality of windows 44a–c, where a window is aligned with each compartment 116a–c of the collection chamber 50.

In addition to defining windows, the mask also includes opaque regions that cover large regions of the front panel. Preferably selected areas of the opaque regions include the indicia provided for calibration or measuring activities. For example, indicia representative of the desired suction pressure to be applied are provided proximate the dry suction control knob 36.

Figure 3A:
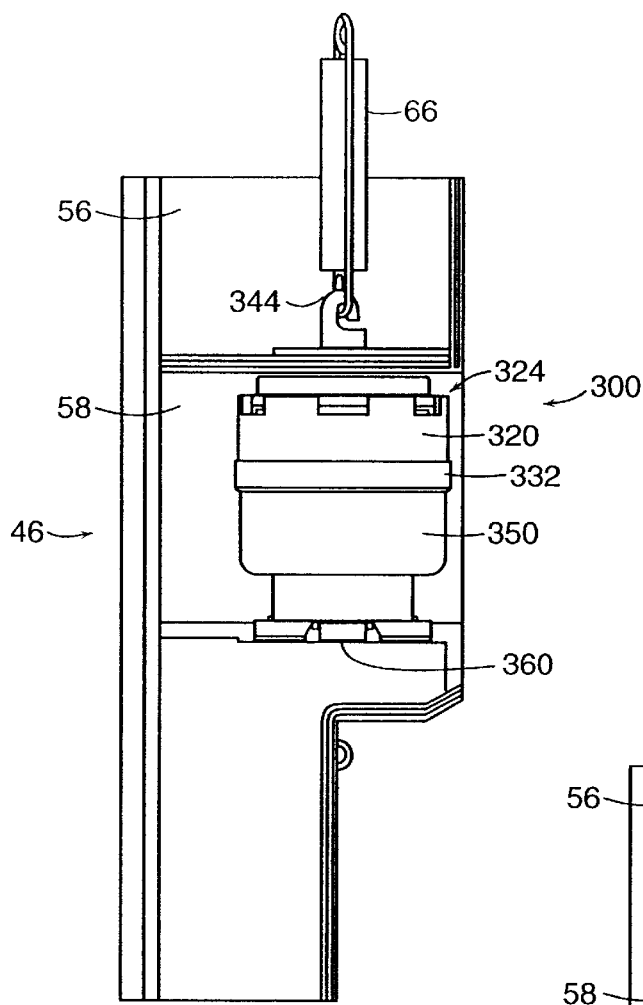
FIG. 3A is a partial cross-sectional front view of the drainage device of FIG. 2 with major portions thereof removed for clarity.
Figure 3B:
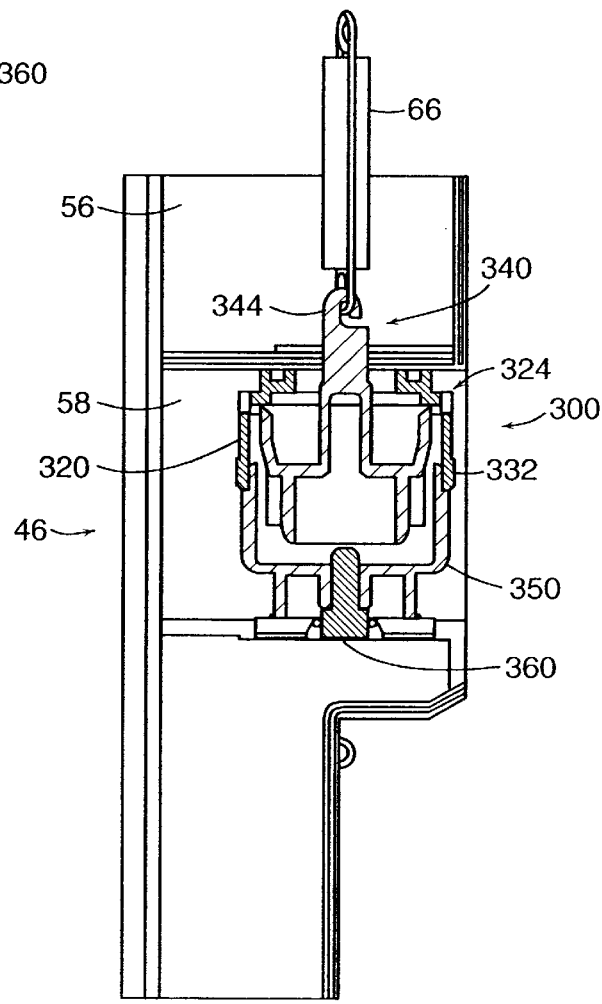
FIG. 3B is a partial cross-sectional view of the drainage device of FIG. 2 with the rolling seal suction pressure regulator shown in cross-section.

The walls, ribs and partitions internal to the device housing 12, as indicated above, are arranged so as to define three internal chambers; a suction pressure regulation chamber 46, an air leak meter chamber 48 and a collection chamber 50. As shown in FIG. 2 and also in FIGS. 3A,B, the suction pressure regulation chamber 46 includes a number of walls and partitions that define a first compartment 56 and a second compartment 58. The upper end of the first compartment 56 has an opening 22 which communicates with the atmosphere and the second compartment 58 is fluidly coupled to the suction port 24.

Figure 4A:
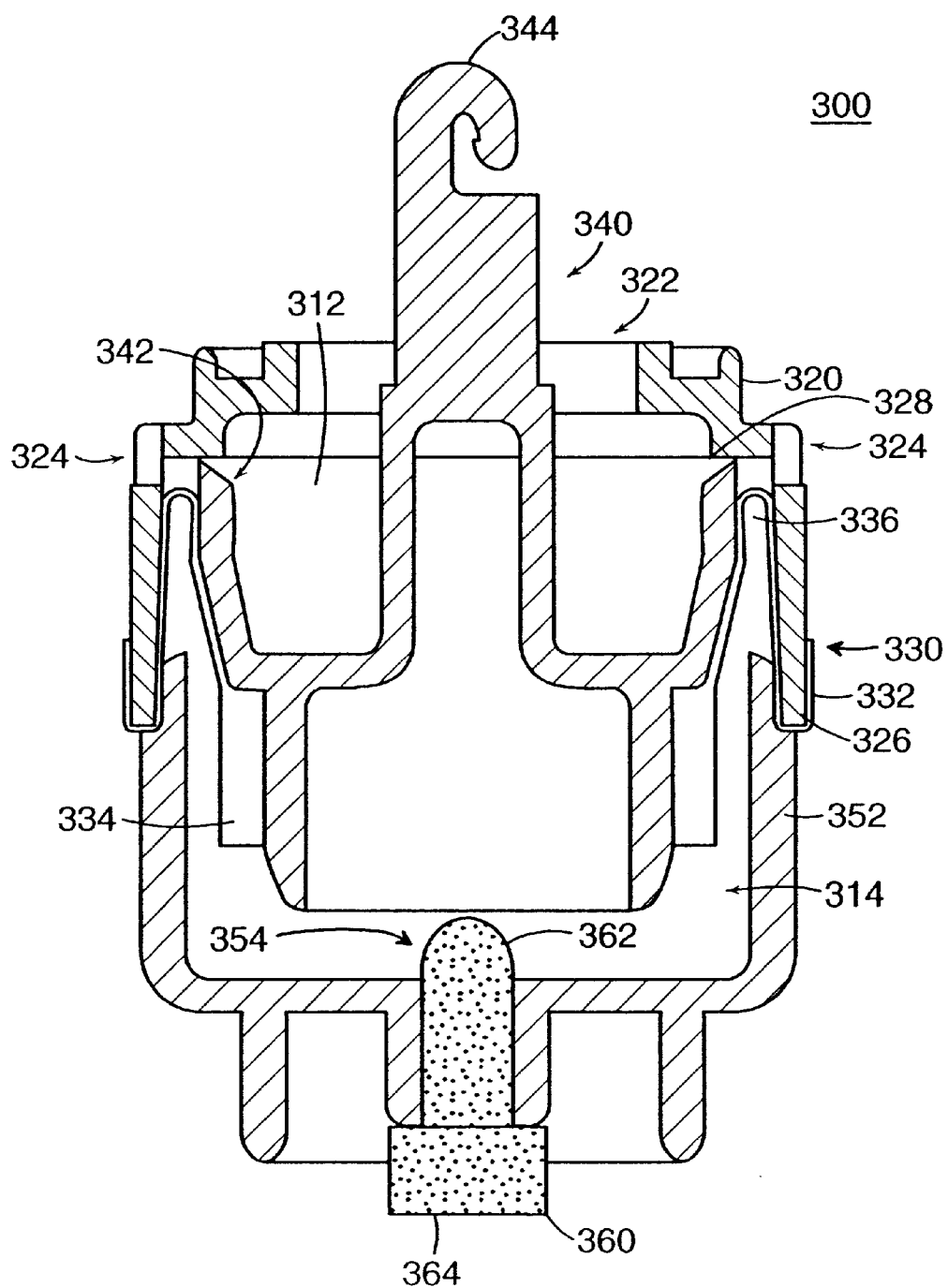
FIG. 4A is a cross-sectional view of the rolling seal suction pressure regulator when in the closed position.
Figure 4B:
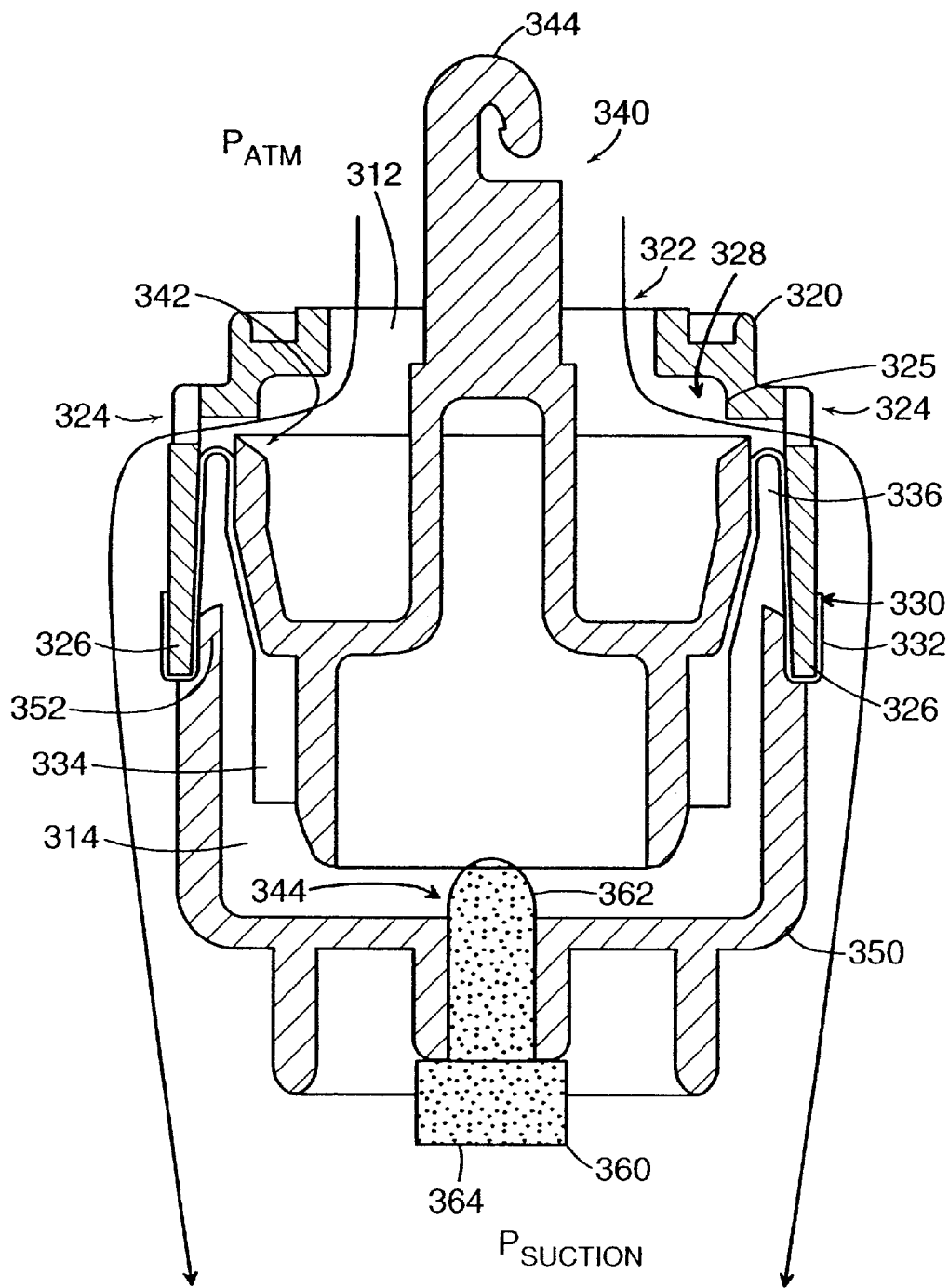
FIG. 4B is a cross-sectional view of a rolling seal suction regulator when in the open position.

Referring now also to FIGS. 4A,B and 5, there are shown cross-sectional views and an exploded view respectively of a rolling seal suction pressure regulator 300 according to a first aspect of the present invention. The rolling seal suction pressure regulator 300 is configured or arranged to control or modulate the suction pressure that is being applied within the rolling seal suction pressure regulator and the suction pressure or degree of vacuum being developed within the drainage device 10. FIG. 4A is illustrative of a rolling seal suction pressure regulator 300 in the closed position and FIG. 4B is illustrative of a rolling seal suction pressure regulator in the open position.

The rolling seal suction pressure regulator 300 includes a top cap 320, a flexible member 330, a poppet 340, a bottom cap 350 and a plug 360. When assembled, the top cap 320, the flexible member 330, the poppet 340 and the bottom cap 350 cooperate so as to subdivide the interior volume of the rolling seal suction pressure regulator into a first or upper interior chamber 312 and a second or lower interior chamber 314.

In an exemplary embodiment, the top cap 320 and bottom cap 350 are generally cylindrically shaped members, however, it is within the scope of the present invention for the top and bottom caps to have any geometric shape.

The rolling seal pressure regulator 300 is disposed in the second compartment 58 of the drainage device 10 and is fluidly interconnected to the first compartment 56. The rolling seal suction pressure regulator 300 also is secured within the second compartment 58 such that the poppet 340 or valve within the rolling seal suction pressure regulator 300 is biased into a closed position by means of a coil spring 66 attached to an end 344 (e.g., hooked end) of the poppet. The coil spring 66 also is secured to one end of a rod 68 whose other end is positioned within a rotatable joint annular collar 70 or coupling that is secured to the housing top 16. The annular collar 70 also includes a key way ridge that is received within a groove along the upper end of the rod 68. In this way, the rod 68 can be rotated together with the collar 70 and simultaneously advanced upwardly or downwardly so as to change the tension in the coil spring 66 that provides the amount of force for seating or sealingly engaging the seating ends 342 of the poppet 340 against the inner seating surface 328 of the top cap 320.

Such tension also corresponds to the amount of suction to be imposed in the collection chamber 50 of the drainage device 10 and likewise in the patient's pleural cavity. As provided in more detail in U.S. Pat. Nos. 4,784,462 and 5,707,734 selective tensioning of the coil spring 66 provides a mechanism by which the drainage device 10 can be configured so a plurality of predetermined, preset suction pressure values are selectable by the user. More particularly, by rotating the dry suction control knob 36 to one of the indicia representative of a desired suction pressure causes the tension in the coil spring 66 and the seating forces developed thereby to be adjusted so the desired suction pressure or degree of vacuum is imposed in the collection chamber.

When the suction pressure or degree of vacuum within the drainage device exceeds the selected or desired suction pressure value, the seating forces developed by the coil spring 66 are overcome and the poppet 340 is moved such that the rolling seal suction pressure regulator 300 is put into the open position or configuration. For further specific details as to the construction and/or operation of the spring biasing means hereinabove described reference should be made to U.S. Pat. Nos. 4,715,855; 4,889,531; 4,784,462; 5,707,734; 5,026,358; 5,300,050; and 5,507,734 the teachings of which are incorporated herein by reference.

The top cap 320 is configured so as to have an input aperture 322, a plurality of output apertures 324, an end connector 326, and an inner seating surface 328. The input aperture 322 is disposed in an end of the top cap 320 and communicates with a portion of the upper interior chamber 312 and the first compartment 56. Although a single aperture is illustrated, it is within the scope of the present invention for the top cap 320 to be configured or arranged so as to provide a plurality, more specifically a multiplicity, of input apertures, the number and size of each being set or established so as to provide a predetermined and desired flow area. Because the input aperture(s) 322 is in fluid communication with the first compartment 56, the input aperture(s) also is fluidly coupled via the opening 22 with the atmosphere.

The plurality of output apertures 324 are arranged about the circumference of the side of the top cap 320 proximate the top cap end and so each output aperture communicates with another portion of the upper interior chamber 312. Each of the plurality of output apertures 324 also are fluidly coupled to the second compartment 58 and thus to the suction source. The number and size of output apertures 324 are set or established so as to provide another predetermined and desired flow area.

The bottom cap 350 includes an end connector 352 and an input port 354 in which is sealingly disposed the plug 360. The end connector 352 is generally configured so as to have a shape or arrangement that complements the top cap end connector 326. In an illustrative embodiment, the bottom cap end connector 352 includes a notched end in which is received the top cap end connector 326. It is within the scope of the present invention, however, for the top and bottom cap end connector 326,352 to be configured with any end connection detail known to those skilled in the art by which the top and bottom caps 320,350 can be secured together in combination with the flexible member distal end portion 332 so as to form an integral structure and a pressure boundary.

The flexible member 330 includes a distal end portion 332, a skirt portion 334 and a flexible portion 336 that interconnects the end portion and the skirt portion. The flexible member skirt portion 334 is configured so as to be generally complementary of the shape of a portion of the outer surface of the poppet 340. Additionally, the inner diameter or cross-section of the flexible member skirt portion 334 is generally established so the skirt portion remains in mechanical and sealing engagement with the poppet outer surface during normal motion of the poppet as hereinafter described responsive to changes in suction pressure in the lower interior chamber 314. In a more specific example, a press fit is established between this portion of the outer surface of the poppet 340 and the skirt portion 334. It also is within the scope of the present invention for the skirt portion 334 to be mechanically secured to the outer surface of the poppet 340 using any of a number of techniques known to those skilled in the art such as securing by means of adhesives, vibration welding or RF welding.

The flexible member distal end portion 332 is configured and has a sufficient flexibility so that it will conform to the shape and configuration of the assembled top cap and bottom cap end connectors 326,352. Preferably, the distal end portion 332 also is configured so that the distal end portion in combination with the flexible portion 336 allows the poppet 340 to move freely with respect to the top and bottom caps 320,350 and without imposing a force that acts on the moving poppet.

In an illustrative embodiment, the distal end portion 332 is in the form of a flexible cylindrical member that is folded around the top cap end connector 326 so as to be in a generally "U" shape as more clearly shown in FIGS. 4A,B. The bottom cap end connector 352 is then mated to the top cap end connector 326 so as to sealingly and mechanically trap the distal end portion 332 of the flexible member 330 therebetween. It also is within the scope of the present invention for that part of the distal end portion 332 that is folded back upon the on the outside surface of the top cap 320 to be relocated so as to be folded upon the outside surface of the bottom cap 350 so the distal end portion 332 is in a "S" shape form.

Preferably, the diameter of the cylindrically shaped distal end portion is set or established so that it is smaller than the outside diameter of either the top cap 320 or the bottom cap 350. In this way, the flexibility of the distal end portion 332 mechanically and elastically secures the distal end portion about the outside surface of the top or bottom caps 320, 352 as illustrated in FIGS. 4A,B.

In this way, the flexible member 330 by means of its sealing engagement with the poppet 340 and the top and bottom caps 320,350 subdivides the interior volume of the rolling seal suction pressure regulator 300 so as to define the upper interior chamber 312 and the lower interior chamber 314. As shown in FIGS. 4A,B, the upper interior chamber 312 can be further divided by means of the poppet 340 depending upon the operable position of the rolling seal suction pressure regulator 300 so as to effectively isolate the top cap input aperture(s) 322 from the top cap output apertures 324.

When the rolling seal suction pressure regulator 300 is in the closed position, as illustrated in FIG. 4A, the seating ends 342 of the poppet 340 are put into sealing engagement with the inner seating surface 328 of the top cap 320. This generally corresponds to the case where the suction pressure applied within the collection chamber 50 is at or below (i.e., less negative) the desired suction pressure. In this arrangement, the upper interior chamber 312 is further subdivided by the poppet 340 so the top cap input aperture(s) 322 is isolated fluidly from each of the top cap output apertures 324.

Conversely, when the rolling seal suction pressure regulator 300 is put in the open position, as illustrated in FIG. 4B, the seating ends 342 of the poppet 340 move away from the inner seating surface 328 of the top cap 320. This generally corresponds to the case where the suction pressure being imposed is greater than the desired suction pressure (i.e., pressure is more negative). Concurrently, the flexible portion 336 automatically reconfigures itself (e.g., rolls) responsive to this motion of the poppet 340 so as to maintain the pressure boundary between the upper and lower interior chambers 312,314.

The flexible portion 366 rolls or reconfigures itself without imposing a force or drag on the motion of the poppet 340 while maintaining the integrity of the pressure boundary described above. More particularly, the flexible portion 366 rolls or re-configures itself essentially without imposing a changing force, that is without imposing a force that would change as a function of the position and/or direction of motion of the poppet 340 as the poppet moves with respect to the inner seating surface 328. In other words, the flexible portion 366 allows the poppet to move with respect to the top cap seating surface 328 without frictional losses or without imposing a spring rate. In this way, motion of the poppet 340 is not dampened by the flexible member 340.

When the rolling seal suction pressure regulator 300 is put into the open position the upper interior chamber 312 is no longer subdivided and the top cap input aperture 322 is fluidly coupled with each of the top cap output apertures 324. Thus, atmospheric air is admitted into the second compartment 58 via the fluidly coupled top cap input and output apertures 322,324 so as to reduce the suction pressure or degree of vacuum being developed within the drainage device 10 and more specifically the collection chamber 50 thereof. As indicated above, the selectively pre-tensioned coil spring 66 provides a means by which the poppet 340 is placed into sealing engagement with the top cap inner seating surface 328 or moved away therefrom when the actual suction pressure exceeds the selected or desired suction pressure.

The plug 360 is sealingly disposed in the bottom cap input port 354 so a first end 362 of the plug is in fluid communication with the lower interior chamber 314 and a second end 364 of the plug is fluidly coupled to the suction port 24 and collection chamber 50 for the drainage device 10. In an illustrative embodiment, the plug second end 364 is configured with a shoulder that engages and rests against an end surface of the bottom cap input port 354. In this way, a user can easily determine that the plug as been properly inserted and such a configuration also provides additional assurances that the plug 360 is not drawn into the lower interior chamber 314.

In a preferred embodiment, the plug 360 is made of a porous material whose porosity is established so as to modulate or control the suction pressure changes being developed in the lower interior chamber 314, as well as to impede flow to or from the lower interior chamber, responsive to suction pressure changes developed within the drainage device 10. More particularly, the plug material has a porosity such that certain types of suction pressure changes (hereinafter "first type of suction pressure changes") occurring within the drainage device do not result in a change in the suction pressure in the lower interior chamber 314 while other types of suction pressure changes (hereinafter "second type of suction pressure changes") cause a change in the suction pressure developed within the lower interior chamber.

In this way, only the second type of suction pressure changes are those which oppose the seating forces developed by the pre-tensioned coil spring 66. If the second type of suction pressure changes overcome the seating forces developed by the coil spring, then the poppet 340 is opened so air can be admitted through the rolling seal suction pressure regulator 300 to the second compartment 58 as illustrated schematically in FIG. 2 and FIG. 4B and described above.

The first type of suction pressure changes, however, do not impose a force that can oppose the seating forces because they do not cause a change in the suction pressure in the lower interior chamber 314. As a result, the rolling seal suction pressure regulator 300 does not change its operable position responsive to first type of suction pressure changes. In other words if the suction pressure regulator 300 is in the closed position it remains in the closed position and if it is in the open position then the poppet 340 remains in the open position, but the poppet is not modulated or stroked by the suction pressure changes.

Thus, the material comprising the plug 360 effectively isolates or filters out certain types of drainage device suction pressure changes, namely the first type of suction pressure changes, while allowing the suction pressure changes of the second type to act on the poppet 340. As provided above, if the suction pressure changes of the second type exceed a desired value, then the poppet 340 is moved responsive to this change so atmospheric air is communicated to the second compartment 58 so as to reduce the suction pressure being developed within the device and collection chamber thereof.

In a more specific embodiment, the porosity of the material comprising the plug 360 is established to impede flow to or from the lower interior chamber 314, and thus impede suction pressure changes therein that would result from high frequency suction pressure changes within the drainage device 10 (i.e., the second type of suction pressure changes). In the present invention high frequency shall be understood to mean suction pressure changes that would occur with a frequency greater than that of naturally occurring physiological changes and environmental changes. In an exemplary illustrative embodiment, high frequency includes suction pressure changes having a frequency of about 60 Hz or more and more specifically a frequency of about 40 Hz or more. The characteristics of the plug material, however, are such that low frequency suction pressure changes within the drainage device (i.e., first type of suction pressure changes), including those resulting from physiological changes of the patient, can cause flow into or out of the lower interior chamber 314 and thus lead to a suction pressure change to be developed therein.

The characteristics of the plug 360 are such as to make it act as a mechanical low pass filter so as to cutoff suction pressure changes that would otherwise cause an unfiltered poppet 340 to move rapidly or vibrate, for example to move rapidly between the open and closed positions. This configuration thus advantageously dampens the high frequency vibratory motion that could lead to unwanted noise from the drainage device while providing a drainage device that can compensate or accommodate a response to suction pressure changes to normal clinical events. Thus, the plug material advantageously allows a fairly constant suction pressure or degree of vacuum to be maintained in the suction side of the drainage device while avoiding rapid cycling of the poppet 340. Additionally, rapid cycling of the poppet 340 or valve member of the rolling seal suction pressure regulator can be attenuated or eliminated without the need of a dampening device such as a dashpot that directly dampens the motion of the valve member as is required in prior art suction pressure regulators referred to above.

In an exemplary embodiment, the plug 360 is made from thermoplastics such as polyethylene, more particularly, a high density polyethylene porous plastic material manufactured by Porex Technologies Corp. In more specific embodiments, the average pore sizes of a plug 360 made from such a high density polyethylene porous plastic material are in the range of from about 40 to about 80 microns and in a more particular embodiment has an average pore size of about 60 microns. It is within the scope of the present invention for the plug 360 to be constructed from any of a number of available porous materials known to those skilled in the art such as metals and ceramics. For such other materials the porosity is such as to attain the effect on flow impediment as described herein.

It is also within the scope of the present invention for the plug 360 to comprise other means for impeding the flow to and from the lower interior chamber 314. In one case a plug according to an alternative embodiment comprises a solid material such as plastic, metal, artificially or naturally occurring gemstones or ceramics in which a hole of a predetermined diameter is drilled therethrough for example by means of a laser. For example, a sapphire that is laser drilled sometimes referred to as a jeweled orifice. In such cases one end of the through hole is in fluid communication with the second compartment 58 and the other end of the through hole communicates with the lower interior chamber 314. The diameter of the through hole is set or established so as to effect an impediment to flow as herein described.

Alternatively, the mechanism for impeding flow can comprise a tortuous flow path such as for example a coiled tubular member of a given length and inner diameter one end of which communicates with the second compartment 58 and the other end communicates with the lower interior chamber 314. In this case, the length and inner diameter are set or established so as to effect the flow impediment as described herein. The foregoing is not an exhaustive listing or description of every means known for impeding flow and thus it is within the scope of the present invention to adapt the above described rolling seal suction pressure regulator to utilize any such other means for effecting a flow impediment and thus regulation and control over the pressure being developed in the lower interior chamber 314. This includes, for example, configuring or arranging a portion of the bottom cap 350 that is in fluid communication with the lower interior chamber 314 to include a means or mechanism for impeding flow to or from the lower interior chamber.

Figure 6:
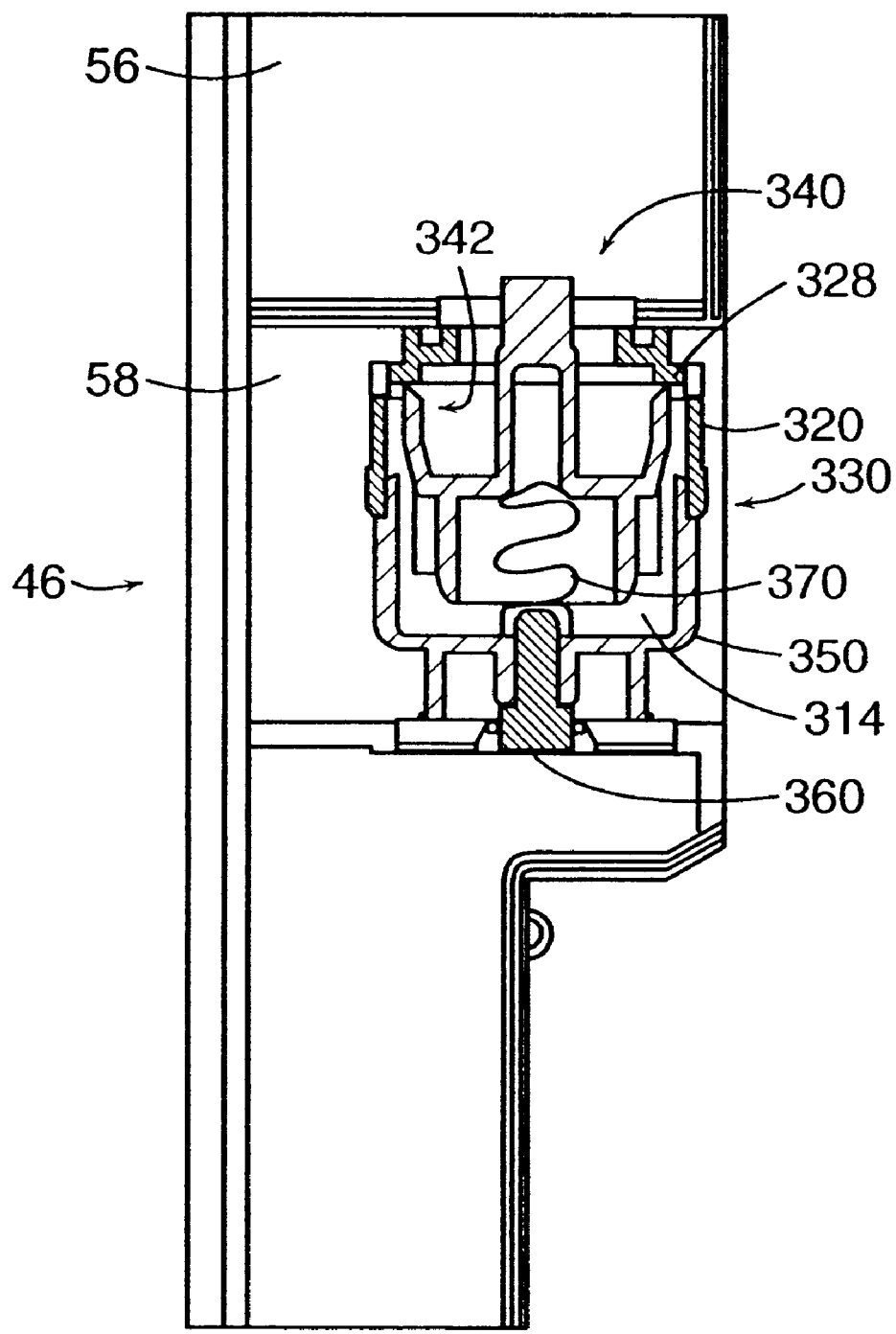
FIG. 6 is a partial cross-sectional front view of a drainage device with major portions thereof removed showing in cross-section a rolling seal suction pressure regulator according to an alternate embodiment of the present invention.

There is shown in FIG. 6, a partial cross-sectional front view of a drainage device similar to that shown in FIG. 2 with major portions thereof removed for clarity and including a rolling seal suction pressure regulator 300*a* according to an alternate embodiment. For this embodiment, the poppet 340 is biased into the closed position by means of a spring 370 that is disposed within the lower interior chamber 314 and between a lower surface of the poppet 340 and a portion of the interior surface of the bottom cap 350. The spring 370, preferably, is pre-compressed to a value corresponding to the predetermined pressure value. Thus, when the suction pressure being developed within the lower interior chamber 314 is at or below (i.e., less negative suction pressure) the desired suction pressure, the spring 370 causes the poppet seating ends 342 to sealingly engage the top cap inner seating surfaces 328.

Figure 5:
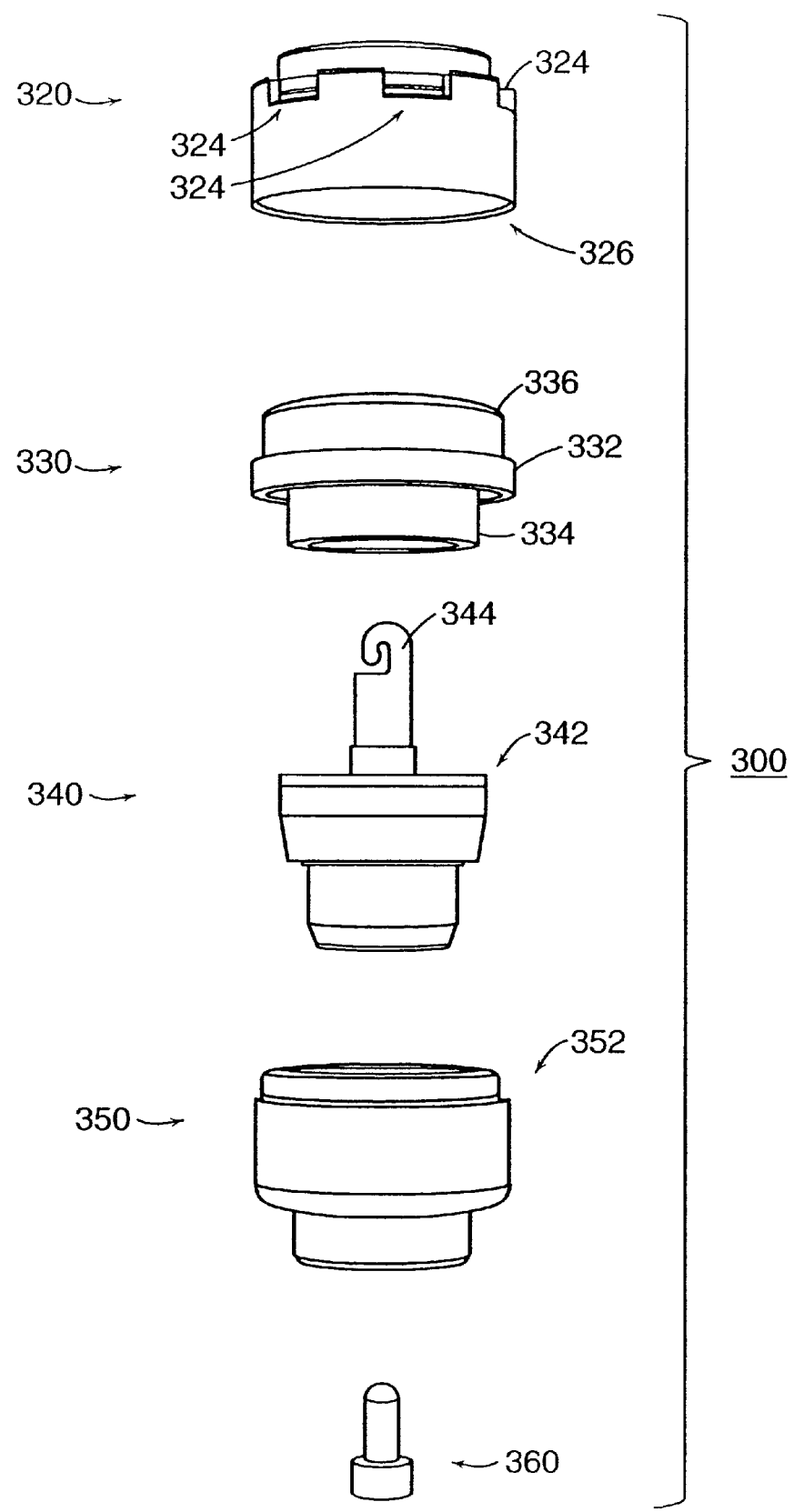
FIG. 5 is an exploded view of the rolling seal suction pressure regulator of FIGS. 2–4.

Conversely, when the suction pressure developed within the lower interior chamber 314 is greater (i.e., more negative) than the desired suction pressure, the spring forces are overcome and the spring 370 is compressed, thus allowing the poppet seating ends 342 to be moved away from the interior seating surface 328. As a result the rolling seal suction pressure regulator 300*a* is put into the open position or condition. As to the other components comprising the rolling seal suction pressure regulator 300*a* of the alternate embodiment, reference shall be made to the above discussion regarding FIGS. 4–5 for the corresponding components.

In the foregoing, there is described a rolling seal suction pressure regulator 300,300*a* according to the present invention used in connection with a drainage device that has a waterless suction pressure regulation means and a dry or waterless patient seal such as the PLEUR-EVAC Sahara S-1100 series made by Genzyeme Surgical Products and including those systems and/or devices described and disclosed in U.S. Pat. Nos. 4,738,671; 4,715,856; 4,554,370; and 4,747,844 and U.S. Ser. No. 08/783,177 the teachings of which are incorporated herein by reference. It is within the scope of the present invention, for either embodiment of the rolling seal suction pressure regulator 300,300*a* of the present invention to be used in connection with any of a number of systems or devices known to those skilled in the art that employ a waterless suction pressure regulation means. This includes a device and system such as the PLEUR-EVAC A-6000 series Adult/Pediatric Chest Drainage and Autotransfusion Systems made by Genzyeme Surgical Products and including those systems and/or devices described and disclosed in U.S. Pat. Nos. 4,695,060; 4,105, 031; 4,784,642; 4,756,501; 4,443,220; 4,955,873; 4,955, 374; and 4,889,531, the teachings of which are incorporated herein by reference.

Figure 7:
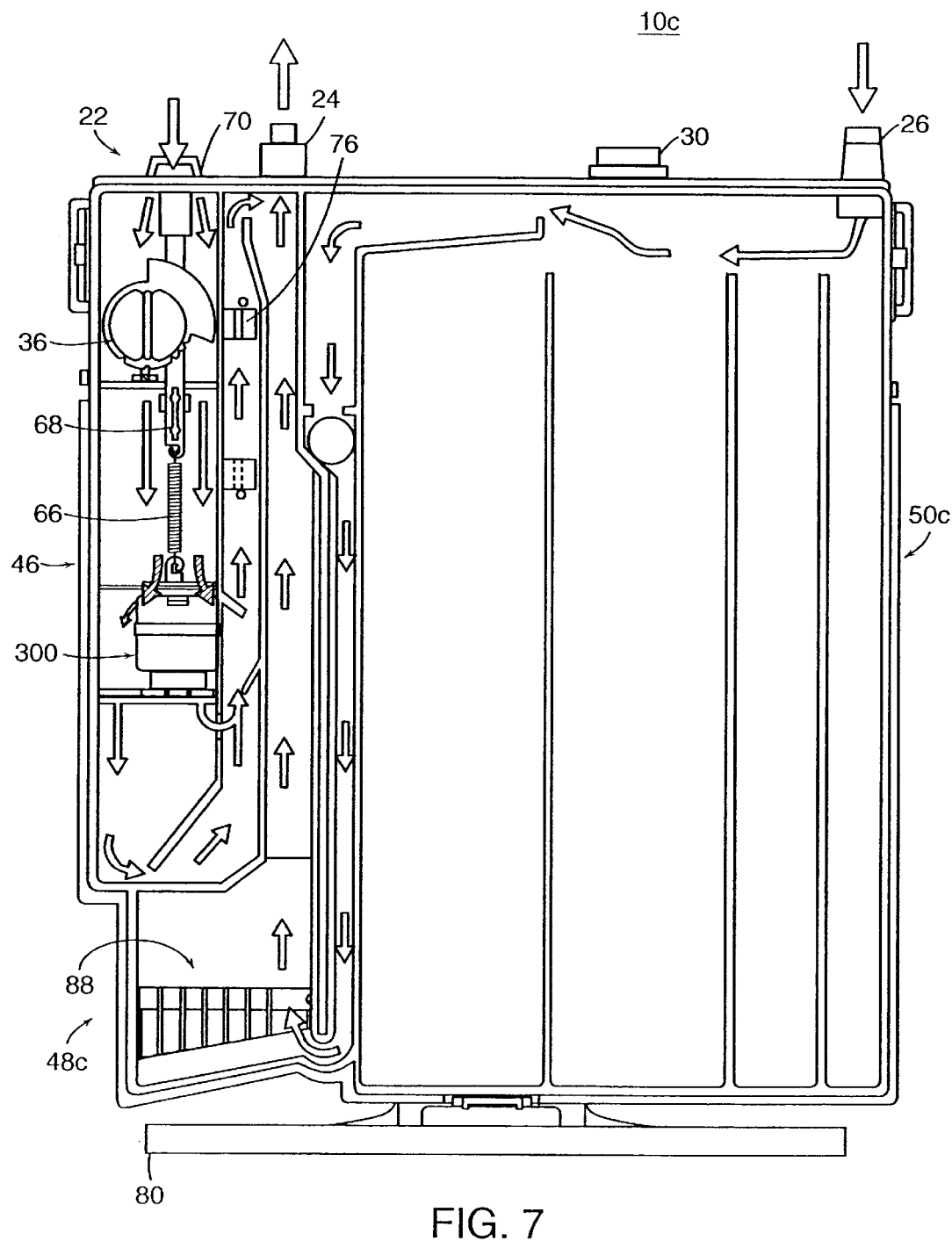
FIG. 7 is a cross-sectional front view of another drainage device according to the present invention with the front panel thereof removed for clarity.

Referring now to FIG. 7, there is shown a cross-sectional front view of another drainage device 10*c* according to the present invention that includes a collection chamber 50*c*, a seal chamber 48*c*, and a suction pressure regulation chamber 46 that includes a rolling seal suction pressure regulator 300. Reference should be made to the forgoing discussion for FIGS. 1–5 for details and operational characteristics of the rolling seal suction pressure regulator 300, the suction pressure regulation chamber 46 and the collection chamber 50*c*. The drainage device 10*c* also more particularly includes a floor stand 380 that is rotatably secured to the main body of the device so the device is self-supporting when put on a flat surface such as a floor.

The seal chamber 48*c*, as with the above described drainage device 10, includes an air leak/flow meter 88. The air leak/flow meter 88 is located in an enlarged cavity at the lower end of the seal chamber 48*c* to measure the amount of gas or air passing through the collection chamber 50*c* to the suction source as well as providing an indication of air leaks between the body cavity and the meter. The seal chamber 48*c* also is configured so as to include a sufficient quantity of a fluid and to provide an adequate fluid level so the seal chamber 48c also constitutes a patient seal. More specific reference should be made to U.S. Pat. No. 4,784,642, the teachings of which are incorporated herein by reference for further details as to such a seal chamber. As such, with this drainage device 10c, the seal chamber 48c is provided to prevent the passage of atmospheric air into the collection chamber 50c.

In the foregoing, the pressure regulator of either embodiment is described with the preferred use of controlling the suction pressure being developed within a drainage device. It is within the scope of the present invention, however, for such a pressure regulator to be utilized to control the pressure of a gas being developed within an apparatus, device or system (e.g., piping system) including positive as well as negative pressures. In such an application, the at least one inlet aperture 322 is fluidly coupled to a first gas source at a first pressure and the at least one outlet aperture 324 and the plug 360 are fluidly coupled to a second gas source at a second pressure. As with the regulator embodiments described hereinabove, when the pressure developed within the lower interior chamber 314 is in the desired range of values, for example is less negative, then the sealing member is maintained in the closed position and if the developed pressure is not within the desired range of values (e.g., more negative) then the sealing member is moved to the open position so the second and first gas sources are fluidly coupled so as to maintain the pressure at or about the desired value.

In addition to the rolling seal suction pressure regulator 300, 300a, either of the drainage devices 10, 10c described herein also can be configured so as to include a unique ventpath arrangement according to another aspect of the present invention. Such a ventpath arrangement is advantageous in that it is particularly configured so as to provide protection from device cross-contamination when the drainage device is inadvertently knocked over and lying on its front or back surface.

For purposes of illustration, this unique ventpath arrangement shall be described with reference to the drainage device as shown in FIG. 2 and also with reference to FIGS. 8–10. The drainage device 10 preferably includes a vent path arrangement that fluidly couples the air leak meter chamber 48 and correspondingly the suction pressure regulation chamber 46 to the collection chamber 50 in a manner that provides protection from cross-contamination when the drainage device is either on its back surface 17 or on the front panel 14b. Preferably, the vent path arrangement includes an intermediate chamber 100 and three passages 102,103,104 that are fluidly coupled thereto. As shown in FIG. 10 the intermediate chamber 100 is sealed with a cover member 101 to prevent the influx of air into the collection chamber 50.

One passage, the first passage 102 fluidly couples the air leak meter chamber 48 with the intermediate chamber 100 and the second and third passages 103,104 fluidly couple the intermediate chamber and the collection chamber 50. These three passages 102,103,104 are arranged so the passages generally extend in a front to back relationship and in a more specific example, are arranged so as to be essentially perpendicular to the surface or plane of the front panel 14b.

Figure 9:
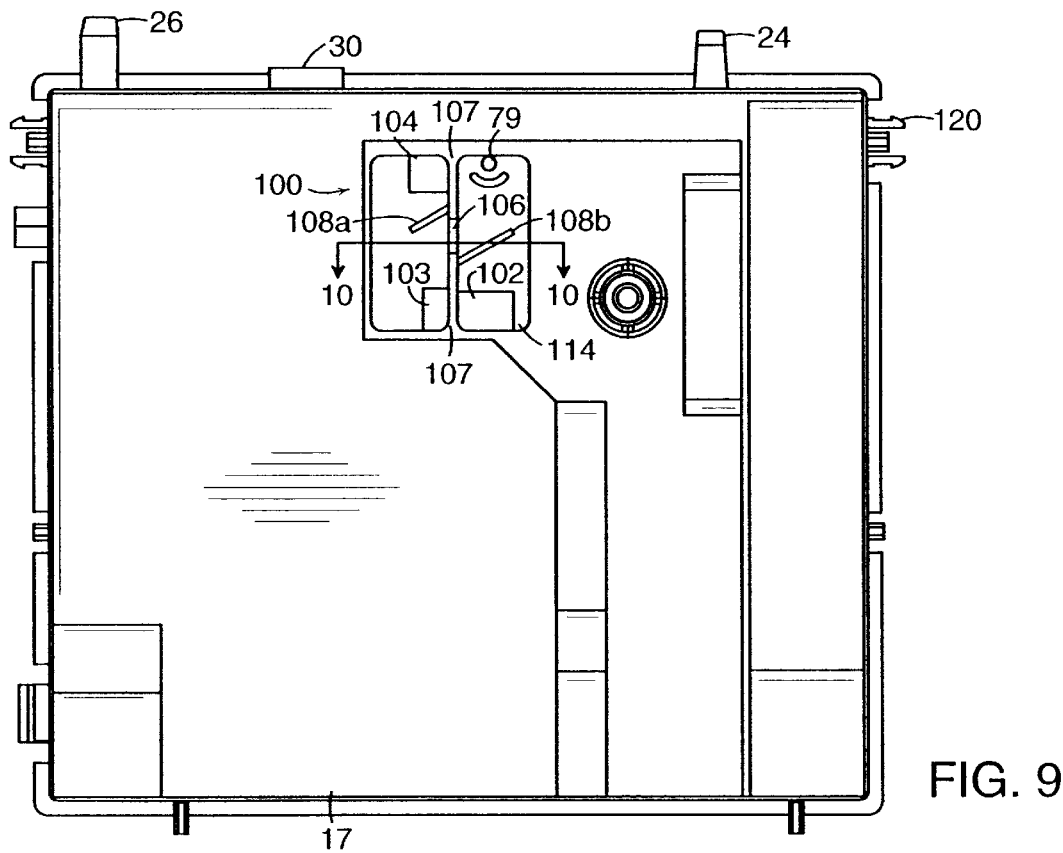
FIG. 9 is an elevation view of the back of the device with the intermediate chamber cover removed for clarity.
Figure 10:
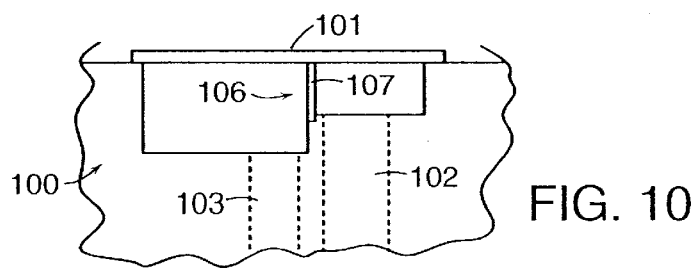
FIG. 10 is a cross-sectional elevation view of the intermediate chamber, taken along section line 10—10 of FIG. 9, with the chamber cover on but the angled members excluded for clarity.

As shown in FIG. 2 and FIG. 9, the three sides for each of these three passages 102,103,104 extend and are sealed to the front panel 14b and the fourth side 110a,110b,110c, respectively of the first, second and third passages are stepped walls spaced from the front panel 14b, so as to form a through opening 112a,112b,112c for each passage. The openings 112b,112c in the second and third passages 103, 104 create a flow path for the gases flowing out of the collection chamber 50 to the suction source via the intermediate chamber 100. The primary vent pathway from the collection chamber 50 is the third passage 104 and the secondary vent pathway is the second passage 103.

During normal operating conditions, the level of fluid in the collection chamber 50 lies well below the openings 112b,112c in the second and third passages 103,104. However, if the drainage device 10 is inadvertently knocked onto its back surface 17, then the level of the liquid in the collection chamber will re-adjust. As such, the fourth sides 110b,110c of the second and third passages 103,104 also are spaced a preset distance from the front panel 14b so the level of the liquid in the collection chamber 50 should lie below the openings 112b,112c when the device is on its back surface.

If the drainage device 10 is inadvertently knocked onto the front panel 14b, the liquid level in the collection chamber also will re-adjust but the openings 112b,112c in the second and third passages 103,104 could be submerged below the liquid level. As such, a liquid level will rise within the second and third passages 103,104 as the level re-adjusts within the collection chamber 50. The liquid level within the second and third passages 103,104 will continue to rise until the liquid from the passages spills over into the intermediate chamber 100 or until the level becomes stabilized in the collection chamber 50. As illustrated in FIGS. 9–10, the intermediate chamber 100 includes a stepped opening 106 so an overflow condition does not immediately result in cross-contamination or cross communication with the first passage 102 and the chamber 48 fluidly connected thereto.

Figure 8:
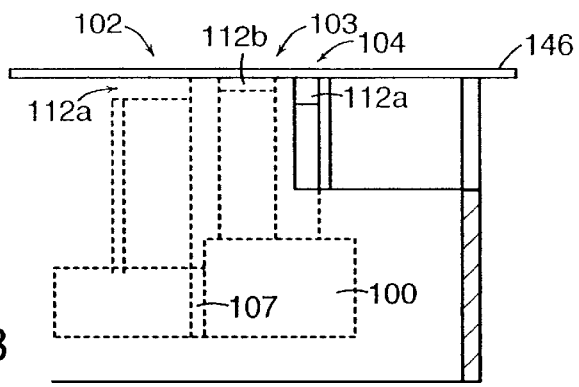
FIG. 8 is an elevation view taken along line 8—8 of FIG. 2 with the front panel on the body portion.

Although FIGS. 8–10 illustrate the two flat surfaces on either side of the partitions 107 as being spaced differently from the cover member 101, this is not a limitation. In an alternate embodiment, the two flat surfaces are equally spaced from the cover member 101 and a stepped wall or partition is provided to establish the intermediate chamber stepped opening 106, e.g., see the stepped partition 114 in the collection chamber 50. It is also within the scope of the instant invention for the two flat surfaces to be equally spaced from the cover member 101 and there be no stepped opening therebetween, but rather just an opening. In this case, the lengths of the second passage 103 and the third passage 104 are selected so the liquid rising in these passages when the device 10 is on its front panel 14b does not spill over into the intermediate chamber 100.

When the drainage device 10 is uprighted, any liquid in the third passage 104, flows into the intermediate chamber 100 and then this liquid, any liquid in the intermediate chamber and any liquid in the second passage 103 flows back into the collection chamber 50 via the second passage. The intermediate chamber also includes two angled members 108a,108b that direct the liquid flowing in the intermediate chamber 100 to the second passage 103 and away from the first passage 102. For example, one of the angled members, member 108a, is angled so the liquid exiting the third passage 104, impinges on the angled member and is directed outwardly away from the first passage 102.

As indicated above, three sides of the first passage 102 extend and are sealed to the front panel 14b and the fourth side 110a is spaced therefrom to create an opening 112a or flow path for the gases passing through the collection chamber 50. The first passage fourth side 110a also is spaced from the front panel so the fluid, if any, in the air leak meter chamber 48 is not communicated to the collection chamber 50 if the drainage device 10 inadvertently falls on its back surface 17. In addition, the small arm of the air leakage chamber 48 is configured so as to retain the fluid volume therein. As with the second and third passages 103,104, the opening 112a formed in the end of the first passage 102 could be submerged below the fluid level if the device 10 falls onto its face panel 14b. However, the volume of the small arm in conjunction with the volume of the first passage 102 is established so the fluid volume used for leak detection and monitoring does not spill over and mix with the fluids in the collection chamber 50.

The drainage device also includes a high negativity relief valve 30, an automatic high negative pressure relief valve 34, a resealable grommet 32, a positive pressure relief valve 28, a float member 76, a negative pressure indicator 80 and an air flow meter 88. The high negativity relief valve 30 is disposed in the housing top 16 and is in fluid communication with the collection chamber 50. The high negativity relief valve 30 includes a button actuated valve which, when depressed, allows filtered air to enter the collection chamber 50. The automatic relief valve 34 is located in the air leak meter chamber 48 and is arranged so it is fluidly coupled to atmosphere through the back 17 of the housing 12. The automatic relief valve 34 also is configured to limit the negative pressure to a predetermined value and to allow filtered air to enter the air leak chamber 48 when actuated.

The resealable grommet 32 is disposed in the housing top 16 and is provided so a user can inject the required volume of a liquid into the air leak meter chamber 32. The positive pressure relief valve 28 also is disposed in the housing top 16 and opens with increased positive pressure in the suction pressure regulation chamber 46. The suction pressure regulation chamber 46 also includes a visual indication to confirm the establishment of a suction pressure condition in the collection chamber. Preferably, the visual indication is supplied by the float member 76 that is slidably disposed in a portion of the second compartment 58.

The negative pressure indicator 80 is located in another compartment provided in the drainage device 10 and is fluidly coupled to the intermediate chamber by means of an aperture 79. Thus, the negative pressure indicator 80 is responsive to the pressure conditions in the collection chamber. In this way, the indicator 80 can provide an indication that there is a negative pressure condition within the collection chamber 50 that is visible to the user in the negative pressure indicator window 42.

As shown in FIG. 2, a plate member having an aperture therein for receiving one end of a one-way valve 84, extends between two plate members. The plate member in conjunction with the one-way valve 84 defines a pressure boundary between the suction pressure regulation chamber 46 and the air leak meter chamber 48 and correspondingly the collection chamber 50. Accordingly, and in an alternate embodiment, a drainage device 10 can be configured with only a suction pressure regulation chamber 46 and a collection chamber 50.

The air leak meter or air flow meter 88 is located in an enlarged cavity provided at the lower end of the air leak meter chamber 48. The air flow meter 88 measures the amount of gas or air passing through the collection chamber 50 to the vacuum pump or vacuum source. In normal operational conditions, the air flow meter 88 provides an indication of the amount of air or gas being evacuated from the body cavity, e.g., pleural cavity, of the patient. The air flow meter 88 also provides an indication of the presence of an air leak somewhere between the body cavity and the flow meter that could be hazardous to a patient's condition if left uncorrected.

For further details regarding the vent path arrangement, the high negativity relief valve 30, automatic high negative pressure relief valve 34, resealable grommet 32, positive pressure relief valve 28, float member 76, negative pressure indicator 80, the air flow meter 88, and components and embodiments thereof, reference shall be made to U.S. Ser. No. 08/783,177 the teaching of which are incorporated by reference herein.

The collection chamber 50 includes two partitions 114, 115 that define three compartments 116a–c. The first compartment 116a communicates with the drain line port 26 and receives the gas and liquid discharges from the drain line 6. Each partition 114,115 includes an aperture 118 so the gaseous discharges are communicated via the first, second and third passages 102,103,104 to the suction source. Each aperture 118 also provides a mechanism for directing the liquids onto the next compartment after the upstream compartment has become filled. Each aperture 118 also is stepped or spaced a preset distance from the front panel 14b as a mechanism for limiting the flow of liquids between compartments 116a,116b,116c when the drainage device 10 is on its back surface 17.

Although a preferred embodiment of the invention has been described using specific terms, such description is for illustrative purposes only, and it is to be understood that changes and variations may be made without departing from the spirit or scope of the following claims.

What is claimed is:

1. A suction pressure regulator comprising:

a housing having an inner surface and at least one inlet aperture and at least one outlet aperture, where each of the at least one inlet aperture is in fluid communication with a source of atmospheric pressure and each or the at least one outlet aperture is in fluid communication with a suction source;

a sealing member moveably disposed within the housing;

a flexible member extending between an outside surface of the sealing member and an inner surface of the housing;

a biasing mechanism wherein the force applied by the biasing mechanism is adjustable and is responsive to suction pressure within at least a portion of the housing and ads on the sealing member so the sealing member is in one of an open position, when the suction pressure within at least a portion of the housing is greater than a predetermined suction pressure value, or a closed position, when the suction pressure therein is at or below the predetermined suction pressure value; and wherein the biasing mechanism is arranged so that in the closed position a sealing portion of the sealing member is urged against an interior surface of the housing so as to obstruct fluid communication between each of the at least one inlet aperture and each of the at least one outlet aperture.

2. The suction pressure regulator according to claim 1, wherein:

the suction pressure regulator is used in combination with a drainage device interconnected to a body cavity and in which a degree of suction pressure is developed within the drainage device by the suction source; and the biasing mechanism is a spring in compressive form that is responsive to physiological induced changes to the degree of vacuum within the drainage device to act on the sealing member to cause the movement thereof between the open position and the closed position.

3. The suction pressure regulator according to claim 1, wherein:
the suction pressure regulator is used in combination with a drainage device interconnected to a body cavity and in which a degree of vacuum is developed within the drainage device by the suction source; and
the biasing mechanism is a spring in an extended form that is responsive to physiological induced changes to the degree of vacuum within the drainage device to act on the sealing member to cause the movement thereof between the open position and the closed position.

4. The suction pressure regulator according to claim 1, wherein the biasing mechanism is a spring that pushes against the sealing member so as to urge the sealing member into sealing engagement with the inner surface of the housing.

5. The suction pressure regulator according to claim 1, wherein the biasing mechanism is a spring that is pre-compressed to a value corresponding to a predetermined suction pressure value.

6. The suction pressure regulator according to claim 1, wherein the biasing mechanism is a spring connected to the sealing member and the spring is pre-tensioned to a value corresponding to a predetermined pressure value.

7. The suction pressure regulator according to claim 1, wherein the biasing mechanism further includes a spring and a spring pro-tensioning adjusting mechanism that selectively pre-tensions the spring to one of a plurality of tension values, each tension value corresponding to one of a plurality of predetermined pressure values.

8. The suction pressure regulator according to claim 1, wherein the flexible member is configured so it does not impose a force on the sealing member as the sealing member moves responsive to the biasing mechanism.

9. The suction pressure regulator according to claim 1, wherein the flexible member is configured so it essentially does not impose a changing force on the sealing member as the sealing member moves responsive to the biasing mechanism.

10. The suction pressure regulator according to claim 1, wherein the flexible member is configured so that motion of the sealing member responsive to the biasing mechanism is essentially frictionless.

11. A suction pressure regulator comprising:
a housing having at least one inlet aperture and at least one outlet aperture, where each of the at least one inlet aperture is in fluid communication with a gas source and each of the at least one outlet aperture is in fluid communication with a suction source;
a sealing member moveably disposed within the housing;
a flexible member extending between an outside surface of the sealing member and an inner surface of the housing;
a biasing mechanism wherein the force applied by the biasing mechanism is adjustable and is responsive to pressure differences in the suction pressure regulator and acts on the sealing member so the sealing member is in one of an open position, when the suction pressure within the housing is greater than a predetermined suction pressure value, or a closed position, when the suction pressure therein is a or below the predetermined suction pressure value; and
wherein the biasing mechanism is arranged so that in the open position the sealing member is moved away from the chamber inner surface whereby each of the at least one inlet aperture is put into fluid communication with each of the at least one outlet aperture and fluid communication between each of the at least one inlet aperture and each of the at least one outlet aperture is obstructed in the closed position thereof.

12. A suction pressure regulator comprising:
a housing having an inner surface and at least one inlet aperture and at least one outlet aperture, where each of the at least one inlet aperture is in fluid communication with a gas source and each of the at least one outlet aperture is in fluid communication with a suction source;
a sealing member moveably disposed within the housing;
a flexible member extending between an outside surface of the scaling member and an inner surface of the housing;
a biasing mechanism that is responsive to suction pressure within the housing and acts on the sealing member so the sealing member is in one of an open position, when the suction pressure within the housing is greater than a predetermined suction pressure value, or a closed position, when the suction pressure therein is at or below the predetermined suction pressure value; and
wherein the flexible member is fixedly attached to at least one of the outside surface of the sealing member and the inner surface of the housing and at least a portion thereof is movable relative to at least one of the outside surface of the sealing member and the inner surface of the housing as the sealing member moves between the closed position and the open position.

13. The suction pressure regulator according to claim 12, wherein: the suction pressure regulator is used in combination with a drainage device interconnected to a body cavity and in which a degree of suction pressure is developed within the drainage device by the suction source; and
the biasing mechanism is a spring in compressive form that is responsive to physiological induced changes to the degree of vacuum within the drainage device to act on the sealing member to cause the movement thereof between the open position and the closed position.

14. The suction pressure regulator according to claim 12, wherein: the suction pressure regulator is used in combination with a drainage device interconnected to a body cavity and in which a degree of vacuum is developed within the drainage device by the suction source; and
the biasing mechanism is a spring in an extended form that is responsive to physiological induced changes to the degree of vacuum within the drainage device to act on the sealing member to cause the movement thereof between the open position and the closed position.

15. The suction pressure regulator according to claim 12, wherein the biasing mechanism is a spring that pushes against the sealing member so as to urge the sealing member into sealing engagement with the inner surface of the housing.

16. The suction pressure regulator according to claim 12, wherein the biasing mechanism is a spring that is pre-compressed to a value corresponding to a predetermined suction pressure value.

17. The suction pressure regulator according to claim 12, wherein the biasing mechanism is a spring connected to the sealing member and the spring is pretensioned to a value corresponding to a predetermined pressure value.

18. The suction pressure regulator according to claim 12, wherein the biasing mechanism further includes a spring and a spring pre-tensioning adjusting mechanism that selectively pre-tensions the spring to one of a plurality of tension values, each tension value corresponding to one of a plurality of predetermined pressure values.

19. The suction pressure regulator according to claim 12, wherein the flexible member is configured so it does not impose a force on the sealing member as the sealing member moves responsive to the biasing mechanism.

20. The suction pressure regulator according to claim 12, wherein the flexible member is configured so it essentially does not impose a changing force on the sealing member as the sealing member moves responsive to the biasing mechanism.

21. The suction pressure regulator according to claim 12, wherein the flexible member is configured so that motion of the sealing member responsive to the biasing mechanism is essentially frictionless.

22. The suction pressure regulator according to claim 12 wherein the flexible member is configured so it does not have a spring rate that opposes motion of the sealing member responsive to the biasing mechanism.

23. An apparatus for draining bodily fluids comprising
a collection chamber for collecting fluids from a body cavity, the collection chamber including an inlet for fluid communication with the body cavity;
a pressure regulation chamber that regulates the degree of vacuum imposed in the collection chamber, the pressure regulating chamber including:
(1) a first compartment being in fluid communication with the collection chamber and having an inlet for coupling to a suction source;
(2) a second compartment having an inlet for communicating with atmospheric pressure; and
(3) a suction pressure regulator including:
(a) a housing having an inner surface and at least one inlet aperture and at least one outlet aperture, where each of the at least one inlet aperture is in fluid communication with the pressure regulation chamber second compartment and each of the at least one outlet aperture is in fluid communication the pressure regulation chamber first compartment;
(b) a sealing member moveably disposed within the housing;
(c) a flexible member extending between an outside surface of the sealing member and an inner surface of the housing; and
(d) a biasing mechanism that is responsive to pressure within the housing second compartment and acts on the sealing member so the sealing member is in one of an open position, when the pressure within the housing second compartment is greater than a predetermined suction pressure value, or a closed position, when the pressure therein is at or below the predetermined suction pressure value, the predetermined suction pressure value corresponding generally to a desired degree of vacuum to be imposed in the collection chamber.

24. The apparatus for draining bodily fluids according to claim 23, wherein for the suction pressure regulator:
(e) the biasing mechanism is arranged so that in the closed position a sealing portion of the sealing member is urged against the inner surface of the housing so as to form a seal between each of the at least one inlet aperture and each of the at least one outlet aperture; and
(f) the biasing mechanism is ranged so that in the open position the sealing member is moved away from the inner surface of the housing whereby each of the at least one inlet aperture is put into fluid communication with each of the at least one outlet aperture.

25. The apparatus for draining bodily fluids according to claim 23, wherein the flexible member is configured so it does not impose a force on the sealing member as the sealing member moves responsive to the biasing mechanism.

26. The apparatus for draining bodily fluids according to claim 23, wherein the flexible member is configured so it essentially does not impose a changing force on the sealing member as the sealing member moves responsive to the biasing mechanism.

27. The apparatus for draining bodily fluids according to claim 23, wherein the flexible member is configured so that motion of the sealing member responsive to the biasing mechanism is essentially frictionless.

28. The apparatus for draining bodily fluids according to claim 23, wherein the flexible member is configured so it does not have a spring rate that opposes motion of the sealing member responsive to the biasing mechanism.

29. The apparatus for draining bodily fluids according to claim 23, wherein the biasing mechanism is a spring that pushes against the sealing member so as to urge the sealing member into sealing engagement with the inner surface of the housing.

30. The apparatus for draining bodily fluids according to claim 29, wherein the spring is pre-compressed to a value corresponding to a desired suction pressure value.

31. The apparatus for draining bodily fluids according to claim 23, wherein the biasing mechanism is a spring connected to the sealing member and the spring is pre-tensioned to a value corresponding to a desired suction pressure value.

32. The apparatus for draining bodily fluids according to claim 23, wherein the biasing mechanism further includes a compressed spring and a spring pretensioning adjusting mechanism that selectively pre-tensions the spring to one of a plurality of tension values, each tension value corresponding to one of a plurality of predetermined suction pressure values.

33. The apparatus for draining bodily fluids according to claim 23, further comprising a seal chamber including a liquid therein to prevent the passage of atmospheric air into the body cavity and being disposed between the pressure regulation chamber and the collection chamber so the suction control chamber first compartment is fluidly coupled to the seal chamber and the collection chamber is fluidly coupled to the seal chamber.

34. The apparatus for draining bodily fluids according to claim 23 further comprising a vent pathway that fluidly couples the pressure regulation chamber and the collection chamber;
wherein the vent pathway includes an intermediate chamber and at least first and second passages, each passage being in fluid communication with the interior of the intermediate chamber;
wherein an opening is provided in the first passage, distal from the intermediate chamber, to fluidly couple the first passage and the pressure regulation chamber;
wherein an opening is provided in the second passage, distal from the intermediate chamber, to fluidly couple the second passage and the collection chamber; and
wherein the first passage and the second passage are arranged so the first and second passages are oriented relative to each other to minimize the passage of fluid therethrough.

35. The apparatus for draining bodily fluids according to claim 34, further comprising a one-way valve disposed within the apparatus so the pressure regulation chamber and the collection chamber are in selective fluid communication with each other by means of the one-way valve, wherein in one position the one-way valve isolates the pressure regulation and collection chambers from each other so gas does not flow to the collection chamber and wherein in another position, the one-way valve puts the chambers in fluid communication with each other so suction pressure from the pressure regulation chamber is applied to the collection chamber to thereby cause the drainage of fluids from a body cavity.

36. An apparatus for draining bodily fluids comprising:

a collection chamber for collecting fluids from a body cavity, the collection chamber including an inlet for fluid communication with the body cavity;

a pressure regulation chamber that regulates the degree of vacuum imposed in flit collection chamber, the pressure regulating chamber including:
  (1) a first compartment being in fluid communication with the collection chamber and having an inlet for coupling to a suction source;
  (2) a second compartment having an inlet for communicating with atmospheric pressure; and
  (3) a suction pressure regulator including:
    (a) a housing having at least one inlet aperture and at least one outlet aperture, where each of the at least one inlet aperture is in fluid communication with the pressure regulation chamber second compartment and each of the at least one outlet aperture is in fluid communication the pressure regulation chamber first compartment;
    (b) a sealing member moveably disposed within the housing;
    (c) a flexible member extending between an outside surface of the sealing member and an inner surface of the housing;
    (d) a biasing mechanism that is responsive to pressure within the housing second compartment and acts on the sealing member so the sealing member is in one of an open position, when the suction pressure within the housing second compartment is greater than a predetermined suction pressure value, or a closed position, when the suction pressure therein is at or below the predetermined value, the predetermined suction pressure value corresponding generally to a desired degree of vacuum to be imposed in the collection chamber;
    (e) wherein the biasing mechanism is arranged so that in the closed position a sealing portion of the sealing member is urged against the housing inner surface so as to form a seal between each of the at least one inlet aperture and each of the at least one outlet aperture;
    (f) wherein the biasing mechanism is arranged so that in the open position the sealing member is moved away from the chamber inner surface whereby each of the at least one inlet aperture is put into fluid communication with each of the at least one outlet aperture.

37. The apparatus for draining bodily fluids according to claim 36, further comprising a seal chamber including a liquid therein to prevent the passage of atmospheric pressure into the body cavity and being disposed between the pressure regulation chamber and the collection chamber so the suction control chamber first compartment is fluidly coupled to the seal chamber and the collection chamber is fluidly coupled to the seal chamber.

38. The apparatus for draining bodily fluids according to claim 36 further comprising a vent pathway that fluidly couples the pressure regulation chamber and the collection chamber;

wherein the vent pathway includes an intermediate chamber and at least first and second passages, each passage being in fluid communication with the interior of the intermediate chamber;

wherein an opening is provided in the first passage, distal from the intermediate chamber, to fluidly couple the first passage and the pressure regulation chamber;

wherein an opening is provided in the second passage, distal from the intermediate chamber, to fluidly couple the second passage and the collection chamber; and wherein the first passage and the second passage are oriented to reduce the flow of fluid therethrough.

39. The apparatus for draining bodily fluids according to claim 38, wherein the first passage and the second passage are arranged so an axis of the first passage and an axis of the second passage are each at angle with respect to a front surface of the apparatus.

40. The apparatus for draining bodily fluids according to claim 38, further comprising a one-way valve disposed within the apparatus so the pressure regulation chamber and the collection chamber are in selective fluid communication with each other by means of the one-way valve, where in one position the one-way valve isolates the pressure regulation and collection chambers from each other so atmospheric pressure does not flow to the collection chamber and where, in another position, the one-way valve puts the chambers in fluid communication with each other so suction pressure from the pressure regulation chamber is applied to the collection chamber to thereby cause the drainage of fluids from a body cavity.

* * * * *